United States Patent
Sundaramurthi et al.

(10) Patent No.: US 11,752,095 B2
(45) Date of Patent: Sep. 12, 2023

(54) MEDROXYPROGESTERONE ACETATE INJECTABLE COMPOSITIONS AND METHODS OF USE

(71) Applicant: Family Health International, Durham, NC (US)

(72) Inventors: Prakash Sundaramurthi, New Hope, PA (US); Ivana Mijakovac, Zagreb (HR); Andrea Rasic, Zagreb (HR); Iva Tunjic, Zagreb (HR)

(73) Assignee: Family Health International, Durham, NC (US)

( * ) Notice: Subject to any disclaimer, the term of this patent is extended or adjusted under 35 U.S.C. 154(b) by 0 days.

(21) Appl. No.: 17/273,392

(22) PCT Filed: Sep. 6, 2019

(86) PCT No.: PCT/IB2019/057537
§ 371 (c)(1),
(2) Date: Mar. 4, 2021

(87) PCT Pub. No.: WO2020/049521
PCT Pub. Date: Mar. 12, 2020

(65) Prior Publication Data
US 2022/0105027 A1   Apr. 7, 2022

Related U.S. Application Data

(60) Provisional application No. 62/728,470, filed on Sep. 7, 2018.

(51) Int. Cl.
*A61K 9/00* (2006.01)
*A61K 31/255* (2006.01)
*A61K 31/566* (2006.01)
*A61K 47/02* (2006.01)
*A61K 47/10* (2017.01)
*A61K 47/20* (2006.01)

(52) U.S. Cl.
CPC .......... *A61K 9/0019* (2013.01); *A61K 31/255* (2013.01); *A61K 31/566* (2013.01); *A61K 47/02* (2013.01); *A61K 47/10* (2013.01); *A61K 47/20* (2013.01)

(58) Field of Classification Search
CPC .. A61K 9/0019; A61K 31/255; A61K 31/566; A61K 47/02; A61K 47/10; A61K 47/20; A61K 31/225; A61K 31/57
See application file for complete search history.

(56) References Cited

U.S. PATENT DOCUMENTS

| | | | |
|---|---|---|---|
| 2004/0039366 A1 | 2/2004 | Macleod | |
| 2009/0004262 A1* | 1/2009 | Shaw | A61K 31/58 424/464 |
| 2013/0183383 A1 | 7/2013 | Phang et al. | |

FOREIGN PATENT DOCUMENTS

| | | |
|---|---|---|
| WO | 01/87266 A1 | 11/2001 |
| WO | 2004/018312 A1 | 3/2004 |
| WO | 2017/149492 A1 | 9/2017 |

OTHER PUBLICATIONS

Anonymous: "depo-subQ provera 104 medroxyprogesterone acetate injectable suspension 104 mg/0.65 ml", Jan. 1, 2015 (Jan. 1, 2015), XP55374545, Retrieved from the Internet: URL:https://dailymed.nlm.nih.gov/dailymed/archives/fdaDrugInfo.cfm? archiveid=168634 [retrieved on May 15, 2017].

Docusate Sodium, A pharmaceutical Guide of Excipients, https://www.pharmaexcipients.com/news/docusate-sodium-a-pharmaceutical-grade-excipient/, 2017 (Year: 2017).

* cited by examiner

*Primary Examiner* — Robert A Wax
*Assistant Examiner* — Quanglong N Truong
(74) *Attorney, Agent, or Firm* — Parker Highlander PLLC

(57) ABSTRACT

The disclosure is directed to medroxyprogesterone compositions suitable for subcutaneous injection comprising about 260 mg/ml to 440 mg/ml medroxyprogesterone acetate, about 0.6 mg/ml to 1.5 mg/ml docusate sodium and, polyethylene glycol. Methods of using these compositions are also described.

22 Claims, 3 Drawing Sheets

MEDROXYPROGESTERONE ACETATE INJECTABLE COMPOSITIONS AND METHODS OF USE

CROSS-REFERENCE TO RELATED APPLICATIONS

This application is the National Stage of International Patent Application No. PCT/IB2019/057537, filed Sep. 6, 2019, which claims the benefit of U.S. Provisional Patent Application No. 62/728,470, filed Sep. 7 2018, the disclosures of which are incorporated herein by reference in their entireties.

TECHNICAL FIELD

The disclosure is directed to long duration medroxyprogesterone acetate compositions for use in regions having extreme conditions such as high heat, high humidity, and unreliable electricity and refrigeration, that are suitable for subcutaneous injection.

BACKGROUND

Medroxyprogesterone acetate (MPA) has been approved in the United States for prevention of pregnancy in women of childbearing potential as well as for the management of endometriosis-associated pain. One such product, Depo-SubQ Provera 104® (medroxyprogesterone acetate injectable suspension) is provided as a single subcutaneous injection of 104 mg once every 12 to 14 weeks. The relatively short duration of action of this product requires four or more medical visits each year, which can impede patient compliance with the treatment protocol.

PCT publications WO2017/149492, WO2019/048906 and WO2019/049081 disclose certain subcutaneous compositions comprising MPA. However, development of a composition having an extended shelf life that can withstand the extreme conditions (e.g. heat up to about 50° C., humidity over 75%, lack of electricity, inadequate refrigeration, and the like) present in many underdeveloped regions and developing countries in which women would benefit from a long acting contraceptive is challenging. A suitable composition having suitable resuspendability, sedimentation rate, viscosity, zeta potential, active pharmaceutical ingredient (API) soluble fraction, particle size distribution (PSD) and/or osmolality to withstand extreme conditions is not described in the art.

There is a need for new formulations of medroxyprogesterone acetate with a longer duration of action and shelf life that can withstand the extreme conditions present in many of the developing countries where longer duration of action formulations are needed.

SUMMARY

Optimized subcutaneous MPA-containing compositions having, e.g., a long duration of action as well as enhanced stability, extended shelf life, and good syringeability and injectability properties are described herein.

The present disclosure is directed to aqueous compositions for subcutaneous injection comprising, e.g., MPA at a concentration of about 260 mg/ml to 440 mg/ml, docusate sodium at a concentration of about 0.6 mg/ml to about 1.5 mg/ml, and polyethylene glycol. Methods of using these compositions are also described.

DETAILED DESCRIPTION OF ILLUSTRATIVE EMBODIMENTS

Figure 1:
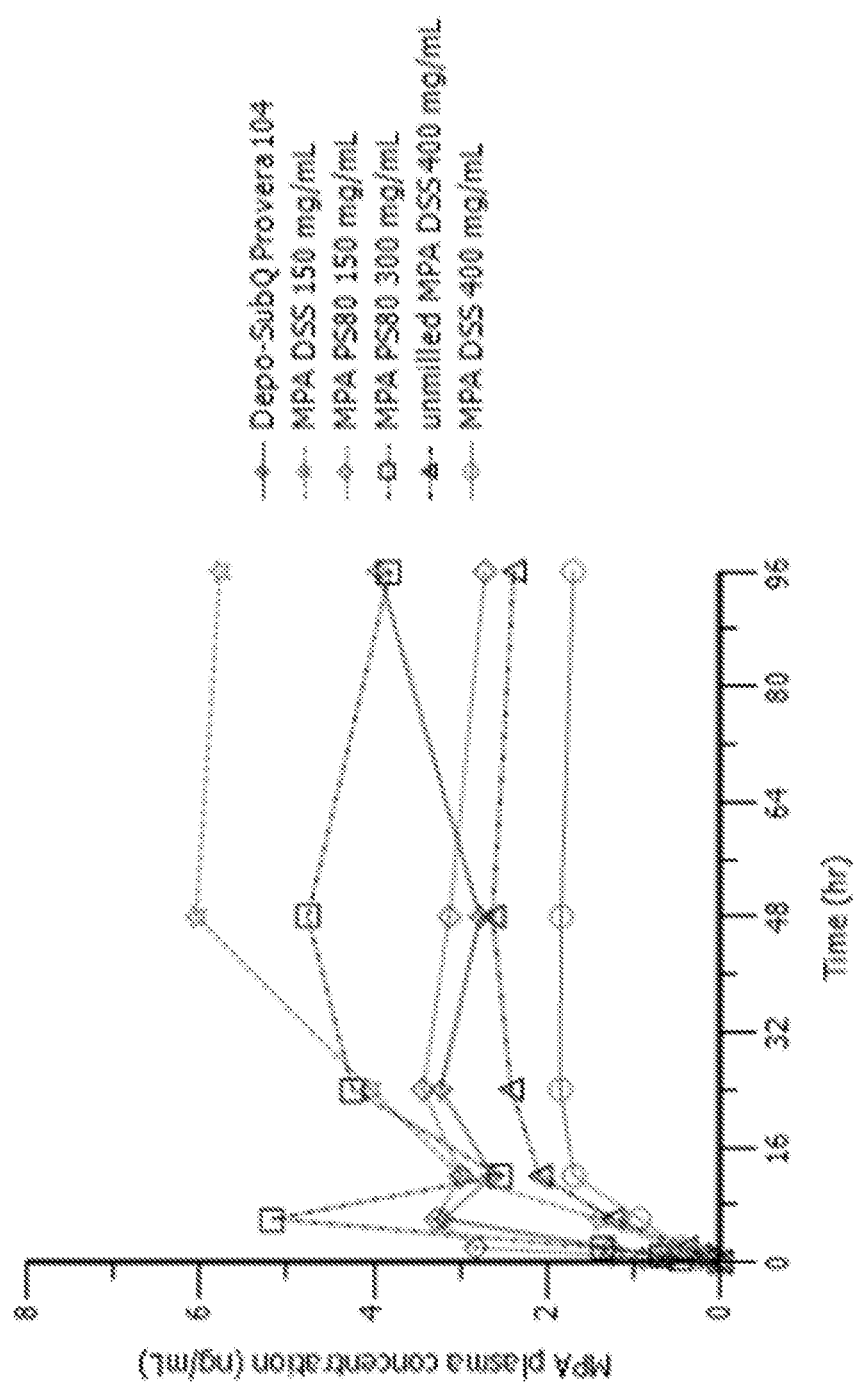
FIG. 1 depicts mean plasma concentration time profiles of medroxyprogesterone acetate in rabbits up to 96 hours postdose.

The present disclosure may be understood more readily by reference to the following detailed description taken in connection with the accompanying figures and examples, which form a part of this disclosure. It is to be understood that this disclosure is not limited to the specific compositions or methods described and/or shown herein, and that the terminology used herein is for the purpose of describing particular embodiments by way of example only and is not intended to be limiting of the claimed disclosure. Also, as used in the specification including the appended claims, the singular forms "a," "an," and "the" include the plural, and reference to a particular numerical value includes at least that particular value, unless the context clearly dictates otherwise. All ranges are inclusive and combinable.

A. General

The modifier "about" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9 to 1.1.

It is to be appreciated that certain features of the disclosure which are, for clarity, described herein in the context of separate embodiments, may also be provided in combination in a single embodiment. Conversely, various features of the disclosure that are, for brevity, described in the context of a single embodiment, may also be provided separately or in any subcombination. Further, reference to values stated in ranges includes each and every value within that range.

As used herein, the term "composition" shall mean a composition that is made under conditions such that it is suitable for administration to humans, e.g., it is made under GMP conditions and contains pharmaceutically acceptable excipients, e.g., without limitation, stabilizers, bulking agents, buffers, carriers, diluents, vehicles, solubilizers, and binders. As used herein pharmaceutical composition includes, but is not limited to, a liquid form ready for subcutaneous injection or infusion. "Composition" and "formulation" are used interchangeably.

The compositions described herein comprise any one or more active pharmaceutical compounds. These active pharmaceutical compounds can include, for example, any agent for which extended release is desired. Such active pharmaceutical compounds can be used for the treatment of infectious diseases, cancer, psychiatric disorders, uterine disorders, and hormonal disorders, as well as for the prevention of pregnancy.

In preferred aspects, the compositions described herein comprise active pharmaceutical ingredients known in the art to be useful for preventing pregnancy or for treating endometriosis-associated pain, renal carcinoma, or endometrial carcinoma in a female patient. The active pharmaceutical ingredient may be selected by one skilled in the art depending on the condition being treated. Selection of the active pharmaceutical ingredient may also depend on other factors including, without limitation, components of the composition, mode of delivery, severity of the condition being treated, the patient's age and weight, and any other active ingredients used in the composition. The compositions may contain one active pharmaceutical ingredient, two active pharmaceutical ingredients, or three or more active pharmaceutical ingredients. For example, the active pharmaceutical ingredient may be estrogen such as ethinyl estradiol or a progestin such as norethindrone, levonorgestrel, desogestrel, ethynidiol diacetate, norgestimate, norenthindrone acetate, norgestrel, drospirenone, norelgestromin or medroxyprogesterone acetate.

In preferred aspects, the compositions described herein for subcutaneous injection comprise medroxyprogesterone acetate. Medroxyprogesterone acetate may also be referred to by one of skill in the art as 6α-6-methyl-3,20-dioxopregna-4-en-17-yl acetate, Pregna-4-ene-3,20-dione, 17-(acetyloxy)-6-methyl,6(α), or 17 alpha-hydroxy-6(α)-methylpregn-4-ene 3,20-dione acetate. Concentrations of medroxyprogesterone acetate in the compositions can range from about 260 mg/ml to 440 mg/ml. For example, the concentrations can range from about 260 mg/ml to 440 mg/ml, 265 mg/ml to 440 mg/ml, 270 mg/ml to 440 mg/ml, 275 mg/ml to 440 mg/ml, 280 mg/ml to 440 mg/ml, 285 mg/ml to 440 mg/ml, 290 mg/ml to 440 mg/ml, 295 mg/ml to 440 mg/ml, 300 mg/ml to 440 mg/ml, 305 mg/ml to 440 mg/ml, 310 mg/ml to 440 mg/ml, 315 mg/ml to 440 mg/ml, 320 mg/ml to 440 mg/ml, 325 mg/ml to 440 mg/ml, 330 mg/ml to 440 mg/ml, 335 mg/ml to 440 mg/ml, 340 mg/ml to 440 mg/ml, 345 mg/ml to 440 mg/ml, 350 mg/ml to 440 mg/ml, 355 mg/ml to 440 mg/ml, 360 mg/ml to 440 mg/ml, 365 mg/ml to 440 mg/ml, 370 mg/ml to 440 mg/ml, 375 mg/ml to 440 mg/ml, 380 mg/ml to 440 mg/ml, 385 mg/ml to 440 mg/ml, 390 mg/ml to 440 mg/ml, 395 mg/ml to 440 mg/ml, 400 mg/ml to 440 mg/ml, 405 mg/ml to 440 mg/ml, 410 mg/ml to 440 mg/ml, 415 mg/ml to 440 mg/ml, 420 mg/ml to 440 mg/ml, 425 mg/ml to 440 mg/ml, 430 mg/ml to 440 mg/ml, 435 mg/ml to 440 mg/ml, 260 mg/ml to 435 mg/ml, 265 mg/ml to 435 mg/ml, 270 mg/ml to 435 mg/ml, 275 mg/ml to 435 mg/ml, 280 mg/ml to 435 mg/ml, 285 mg/ml to 435 mg/ml, 290 mg/ml to 435 mg/ml, 295 mg/ml to 435 mg/ml, 300 mg/ml to 435 mg/ml, 305 mg/ml to 435 mg/ml, 310 mg/ml to 435 mg/ml, 315 mg/ml to 435 mg/ml, 320 mg/ml to 435 mg/ml, 325 mg/ml to 435 mg/ml, 330 mg/ml to 435 mg/ml, 335 mg/ml to 435 mg/ml, 340 mg/ml to 435 mg/ml, 345 mg/ml to 435 mg/ml, 350 mg/ml to 435 mg/ml, 355 mg/ml to 435 mg/ml, 360 mg/ml to 435 mg/ml, 365 mg/ml to 435 mg/ml, 370 mg/ml to 435 mg/ml, 375 mg/ml to 435 mg/ml, 380 mg/ml to 435 mg/ml, 385 mg/ml to 435 mg/ml, 390 mg/ml to 435 mg/ml, 395 mg/ml to 435 mg/ml, 400 mg/ml to 435 mg/ml, 405 mg/ml to 435 mg/ml, 410 mg/ml to 435 mg/ml, 415 mg/ml to 435 mg/ml, 420 mg/ml to 435 mg/ml, 425 mg/ml to 435 mg/ml, 430 mg/ml to 435 mg/ml, 260 mg/ml to 430 mg/ml, 265 mg/ml to 430 mg/ml, 270 mg/ml to 430 mg/ml, 275 mg/ml to 430 mg/ml, 280 mg/ml to 430 mg/ml, 285 mg/ml to 430 mg/ml, 290 mg/ml to 430 mg/ml, 295 mg/ml to 430 mg/ml, 300 mg/ml to 430 mg/ml, 305 mg/ml to 430 mg/ml, 310 mg/ml to 430 mg/ml, 315 mg/ml to 430 mg/ml, 320 mg/ml to 430 mg/ml, 325 mg/ml to 430 mg/ml, 330 mg/ml to 430 mg/ml, 335 mg/ml to 430 mg/ml, 340 mg/ml to 430 mg/ml, 345 mg/ml to 430 mg/ml, 350 mg/ml to 430 mg/ml, 355 mg/ml to 430 mg/ml, 360 mg/ml to 430 mg/ml, 365 mg/ml to 430 mg/ml, 370 mg/ml to 430 mg/ml, 375 mg/ml to 430 mg/ml, 380 mg/ml to 430 mg/ml, 385 mg/ml to 430 mg/ml, 390 mg/ml to 430 mg/ml, 395 mg/ml to 430 mg/ml, 400 mg/ml to 430 mg/ml, 405 mg/ml to 430 mg/ml, 410 mg/ml to 430 mg/ml, 415 mg/ml to 430 mg/ml, 420 mg/ml to 430 mg/ml, 425 mg/ml to 430 mg/ml, 260 mg/ml to 425 mg/ml, 265 mg/ml to 425 mg/ml, 270 mg/ml to 425 mg/ml, 275 mg/ml to 425 mg/ml, 280 mg/ml to 425 mg/ml, 285 mg/ml to 425 mg/ml, 290 mg/ml to 425 mg/ml, 295 mg/ml to 425 mg/ml, 300 mg/ml to 425 mg/ml, 305 mg/ml to 425 mg/ml, 310 mg/ml to 425 mg/ml, 315 mg/ml to 425 mg/ml, 320 mg/ml to 425 mg/ml, 325 mg/ml to 425 mg/ml, 330 mg/ml to 425 mg/ml, 335 mg/ml to 425 mg/ml, 340 mg/ml to 425 mg/ml, 345 mg/ml to 425 mg/ml, 350 mg/ml to 425 mg/ml, 355 mg/ml to 425 mg/ml, 360 mg/ml to 425 mg/ml, 365 mg/ml to 425 mg/ml, 370 mg/ml to 425 mg/ml, 375 mg/ml to 425 mg/ml, 380 mg/ml to 425 mg/ml, 385 mg/ml to 425 mg/ml, 390 mg/ml to 425 mg/ml, 395 mg/ml to 425 mg/ml, 400 mg/ml to 425 mg/ml, 405 mg/ml to 425 mg/ml, 410 mg/ml to 425 mg/ml, 415 mg/ml to 425 mg/ml, 420 mg/ml to 425 mg/ml, 260 mg/ml to 420 mg/ml, 265 mg/ml to 420 mg/ml, 270 mg/ml to 420 mg/ml, 275 mg/ml to 420 mg/ml, 280 mg/ml to 420 mg/ml, 285 mg/ml to 420 mg/ml, 290 mg/ml to 420 mg/ml, 295 mg/ml to 420 mg/ml, 300 mg/ml to 420 mg/ml, 305 mg/ml to 420 mg/ml, 310 mg/ml to 420 mg/ml, 315 mg/ml to 420 mg/ml, 320 mg/ml to 420 mg/ml, 325 mg/ml to 420 mg/ml, 330 mg/ml to 420 mg/ml, 335 mg/ml to 420 mg/ml, 340 mg/ml to 420 mg/ml, 345 mg/ml to 420 mg/ml, 350 mg/ml to 420 mg/ml, 355 mg/ml to 420 mg/ml, 360 mg/ml to 420 mg/ml, 365 mg/ml to 420 mg/ml, 370 mg/ml to 420 mg/ml, 375 mg/ml to 420 mg/ml, 380 mg/ml to 420 mg/ml, 385 mg/ml to 420 mg/ml, 390 mg/ml to 420 mg/ml, 395 mg/ml to 420 mg/ml, 400 mg/ml to 420 mg/ml, 405 mg/ml to 420 mg/ml, 410 mg/ml to 420 mg/ml, 415 mg/ml to 420 mg/ml, 260 mg/ml to 415 mg/ml, 265 mg/ml to 415 mg/ml, 270 mg/ml to 415 mg/ml, 275 mg/ml to 415 mg/ml, 280 mg/ml to 415 mg/ml, 285 mg/ml to 415 mg/ml, 290 mg/ml to 415 mg/ml, 295 mg/ml to 415 mg/ml, 300 mg/ml to 415 mg/ml, 305 mg/ml to 415 mg/ml, 310 mg/ml to 415 mg/ml, 315 mg/ml to 415 mg/ml, 320 mg/ml to 415 mg/ml, 325 mg/ml to 415 mg/ml, 330 mg/ml to 415 mg/ml, 335 mg/ml to 415 mg/ml, 340 mg/ml to 415 mg/ml, 345 mg/ml to 415 mg/ml, 350 mg/ml to 415 mg/ml, 355 mg/ml to 415 mg/ml, 360 mg/ml to 415 mg/ml, 365 mg/ml to 415 mg/ml, 370 mg/ml to 415 mg/ml, 375 mg/ml to 415 mg/ml, 380 mg/ml to 415 mg/ml, 385 mg/ml to 415 mg/ml, 390 mg/ml to 415 mg/ml, 395 mg/ml to 415 mg/ml, 400 mg/ml to 415 mg/ml, 405 mg/ml to 415 mg/ml, 410 mg/ml to 415 mg/ml, 260 mg/ml to 410 mg/ml, 265 mg/ml to 410 mg/ml, 270 mg/ml to 410 mg/ml, 275 mg/ml to 410 mg/ml, 280 mg/ml to 410 mg/ml, 285 mg/ml to 410 mg/ml, 290 mg/ml to 410 mg/ml, 295 mg/ml to 410 mg/ml, 300 mg/ml to 410 mg/ml, 305 mg/ml to 410 mg/ml, 310 mg/ml to 410 mg/ml, 315 mg/ml to 410 mg/ml, 320 mg/ml to 410 mg/ml, 325 mg/ml to 410 mg/ml, 330 mg/ml to 410 mg/ml, 335 mg/ml to 410 mg/ml, 340 mg/ml to 410 mg/ml, 345 mg/ml to 410 mg/ml, 350 mg/ml to 410 mg/ml, 355 mg/ml to 410 mg/ml, 360 mg/ml to 410 mg/ml, 365 mg/ml to 410 mg/ml, 370 mg/ml to 410 mg/ml, 375 mg/ml to 410 mg/ml, 380 mg/ml to 410 mg/ml, 385 mg/ml to 410 mg/ml, 390 mg/ml to 410 mg/ml, 395 mg/ml to 410 mg/ml, 400 mg/ml to 410 mg/ml, 405 mg/ml to 410 mg/ml, 260 mg/ml to 405 mg/ml, 265 mg/ml to 405 mg/ml, 270 mg/ml to 405 mg/ml, 275 mg/ml to 405 mg/ml, 280 mg/ml to 405 mg/ml, 285 mg/ml to 405 mg/ml, 290 mg/ml to 405 mg/ml, 295 mg/ml to 405 mg/ml, 300 mg/ml to 405 mg/ml, 305 mg/ml to 405 mg/ml, 310 mg/ml to 405 mg/ml, 315 mg/ml to 405 mg/ml, 320 mg/ml to 405 mg/ml, 325 mg/ml to 405 mg/ml, 330 mg/ml to 405 mg/ml, 335 mg/ml to 405 mg/ml, 340 mg/ml to 405 mg/ml, 345 mg/ml to 405 mg/ml, 350 mg/ml to 405 mg/ml, 355 mg/ml to 405 mg/ml, 360 mg/ml to 405 mg/ml, 365 mg/ml to 405 mg/ml, 370 mg/ml to 405 mg/ml, 375 mg/ml to 405 mg/ml, 380 mg/ml to 405 mg/ml, 385 mg/ml to 405 mg/ml, 390 mg/ml to 405 mg/ml, 395 mg/ml to 405 mg/ml, 260 mg/ml to 400 mg/ml, 265 mg/ml to 400 mg/ml, 270 mg/ml to 400 mg/ml, 275 mg/ml to 400 mg/ml, 280 mg/ml to 400 mg/ml, 285 mg/ml to 400 mg/ml, 290 mg/ml to 400 mg/ml, 295 mg/ml to 400 mg/ml, 300 mg/ml to 400 mg/ml, 305 mg/ml to 400 mg/ml, 310 mg/ml to 400 mg/ml, 315 mg/ml to 400 mg/ml, 320 mg/ml to 400 mg/ml, 325 mg/ml to 400 mg/ml, 330 mg/ml to 400 mg/ml, 335 mg/ml to 400 mg/ml, 340 mg/ml to 400 mg/ml, 345 mg/ml to 400 mg/ml, 350 mg/ml to 400 mg/ml, 355 mg/ml to 400 mg/ml, 360 mg/ml to 400 mg/ml, 365 mg/ml to 400 mg/ml, 370 mg/ml to 400 mg/ml, 375 mg/ml to 400 mg/ml, 380 mg/ml to 400 mg/ml, 385 mg/ml to 400 mg/ml, 390 mg/ml to 400 mg/ml, 395 mg/ml to 400 mg/ml, 260 mg/ml to 395 mg/ml, 265 mg/ml to 395 mg/ml, 270 mg/ml to 395 mg/ml, 275 mg/ml to 395 mg/ml, 280 mg/ml to 395 mg/ml, 285 mg/ml to 395 mg/ml, 290 mg/ml to 395 mg/ml, 295 mg/ml to 395 mg/ml, 300 mg/ml to 395 mg/ml, 305 mg/ml to 395 mg/ml, 310 mg/ml to 395 mg/ml, 315 mg/ml to 395 mg/ml, 320 mg/ml to 395 mg/ml, 325 mg/ml to 395 mg/ml, 330 mg/ml to 395 mg/ml, 335 mg/ml to 395 mg/ml, 340 mg/ml to 395 mg/ml, 345 mg/ml to 395 mg/ml, 350 mg/ml to 395 mg/ml, 355 mg/ml to 395 mg/ml, 360 mg/ml to 395 mg/ml, 365 mg/ml to 395 mg/ml, 370 mg/ml to 395 mg/ml, 375 mg/ml to 395 mg/ml, 380 mg/ml to 395 mg/ml, 385 mg/ml to 395 mg/ml, 390 mg/ml to 395 mg/ml, 260 mg/ml to 390 mg/ml, 265 mg/ml to 390 mg/ml, 270 mg/ml to 390 mg/ml, 275 mg/ml to 390 mg/ml, 280 mg/ml to 390 mg/ml, 285 mg/ml to 390 mg/ml, 290 mg/ml to 390 mg/ml, 295 mg/ml to 390 mg/ml, 300 mg/ml to 390 mg/ml, 305 mg/ml to 390 mg/ml, 310 mg/ml to 390 mg/ml, 315 mg/ml to 390 mg/ml, 320 mg/ml to 390 mg/ml, 325 mg/ml to 390 mg/ml, 330 mg/ml to 390 mg/ml, 335 mg/ml to 390 mg/ml, 340 mg/ml to 390 mg/ml, 345 mg/ml to 390 mg/ml, 350 mg/ml to 390 mg/ml, 355 mg/ml to 390 mg/ml, 360 mg/ml to 390 mg/ml, 365 mg/ml to 390 mg/ml, 370 mg/ml to 390 mg/ml, 375 mg/ml to 390 mg/ml, 380 mg/ml to 390 mg/ml, 385 mg/ml to 390 mg/ml, 260 mg/ml to 385 mg/ml, 265 mg/ml to 385 mg/ml, 270 mg/ml to 385 mg/ml, 275 mg/ml to 385 mg/ml, 280 mg/ml to 385 mg/ml, 285 mg/ml to 385 mg/ml, 290 mg/ml to 385 mg/ml, 295 mg/ml to 385 mg/ml, 300 mg/ml to 385 mg/ml, 305 mg/ml to 385 mg/ml, 310 mg/ml to 385 mg/ml, 315 mg/ml to 385 mg/ml, 320 mg/ml to 385 mg/ml, 325 mg/ml to 385 mg/ml, 330 mg/ml to 385 mg/ml, 335 mg/ml to 385 mg/ml, 340 mg/ml to 385 mg/ml, 345 mg/ml to 385 mg/ml, 350 mg/ml to 385 mg/ml, 355 mg/ml to 385 mg/ml, 360 mg/ml to 385 mg/ml, 365 mg/ml to 385 mg/ml, 370 mg/ml to 385 mg/ml, 375 mg/ml to 385 mg/ml, 380 mg/ml to 385 mg/ml, 260 mg/ml to 380 mg/ml, 265 mg/ml to 380 mg/ml, 270 mg/ml to 380 mg/ml, 275 mg/ml to 380 mg/ml, 280 mg/ml to 380 mg/ml, 285 mg/ml to 380 mg/ml, 290 mg/ml to 380 mg/ml, 295 mg/ml to 380 mg/ml, 300 mg/ml to 380 mg/ml, 305 mg/ml to 380 mg/ml, 310 mg/ml to 380 mg/ml, 315 mg/ml to 380 mg/ml, 320 mg/ml to 380 mg/ml, 325 mg/ml to 380 mg/ml, 330 mg/ml to 380 mg/ml, 335 mg/ml to 380 mg/ml, 340 mg/ml to 380 mg/ml, 345 mg/ml to 380 mg/ml, 350 mg/ml to 380 mg/ml, 355 mg/ml to 380 mg/ml, 360 mg/ml to 380 mg/ml, 365 mg/ml to 380 mg/ml, 370 mg/ml to 380 mg/ml, 375 mg/ml to 380 mg/ml, 260 mg/ml to 375 mg/ml, 265 mg/ml to 375 mg/ml, 270 mg/ml to 375 mg/ml, 275 mg/ml to 375 mg/ml, 280 mg/ml to 375 mg/ml, 285 mg/ml to 375 mg/ml, 290 mg/ml to 375 mg/ml, 295 mg/ml to 375 mg/ml, 300 mg/ml to 375 mg/ml, 305 mg/ml to 375 mg/ml, 310 mg/ml to 375 mg/ml, 315 mg/ml to 375 mg/ml, 320 mg/ml to 375 mg/ml, 325 mg/ml to 375 mg/ml, 330 mg/ml to 375 mg/ml, 335 mg/ml to 375 mg/ml, 340 mg/ml to 375 mg/ml, 345 mg/ml to 375 mg/ml, 350 mg/ml to 375 mg/ml, 355 mg/ml to 375 mg/ml, 360 mg/ml to 375 mg/ml, 365 mg/ml to 375 mg/ml, 370 mg/ml to 375 mg/ml, 260 mg/ml to 370 mg/ml, 265 mg/ml to 370 mg/ml, 270 mg/ml to 370 mg/ml, 275 mg/ml to 370 mg/ml, 280 mg/ml to 370 mg/ml, 285 mg/ml to 370 mg/ml, 290 mg/ml to 370 mg/ml, 295 mg/ml to 370 mg/ml, 300 mg/ml to 370 mg/ml, 305 mg/ml to 370 mg/ml, 310 mg/ml to 370 mg/ml, 315 mg/ml to 370 mg/ml, 320 mg/ml to 370 mg/ml, 325 mg/ml to 370 mg/ml, 330 mg/ml to 370 mg/ml, 335 mg/ml to 370 mg/ml, 340 mg/ml to 370 mg/ml, 345 mg/ml to 370 mg/ml, 350 mg/ml to 370 mg/ml, 355 mg/ml to 370 mg/ml, 360 mg/ml to 370 mg/ml, 365 mg/ml to 370 mg/ml, 260 mg/ml to 365 mg/ml, 265 mg/ml to 365 mg/ml, 270 mg/ml to 365 mg/ml, 275 mg/ml to 365 mg/ml, 280 mg/ml to 365 mg/ml, 285 mg/ml to 365 mg/ml, 290 mg/ml to 365 mg/ml, 295 mg/ml to 365 mg/ml, 300 mg/ml to 365 mg/ml, 305 mg/ml to 365 mg/ml, 310 mg/ml to 365 mg/ml, 315 mg/ml to 365 mg/ml, 320 mg/ml to 365 mg/ml, 325 mg/ml to 365 mg/ml, 330 mg/ml to 365 mg/ml, 335 mg/ml to 365 mg/ml, 340 mg/ml to 365 mg/ml, 345 mg/ml to 365 mg/ml, 350 mg/ml to 365 mg/ml, 355 mg/ml to 365 mg/ml, 360 mg/ml to 365 mg/ml, 260 mg/ml to 360 mg/ml, 265 mg/ml to 360 mg/ml, 270 mg/ml to 360 mg/ml, 275 mg/ml to 360 mg/ml, 280 mg/ml to 360 mg/ml, 285 mg/ml to 360 mg/ml, 290 mg/ml to 360 mg/ml, 295 mg/ml to 360 mg/ml, 300 mg/ml to 360 mg/ml, 305 mg/ml to 360 mg/ml, 310 mg/ml to 360 mg/ml, 315 mg/ml to 360 mg/ml, 320 mg/ml to 360 mg/ml, 325 mg/ml to 360 mg/ml, 330 mg/ml to 360 mg/ml, 335 mg/ml to 360 mg/ml, 340 mg/ml to 360 mg/ml, 345 mg/ml to 360 mg/ml, 350 mg/ml to 360 mg/ml, 355 mg/ml to 360 mg/ml, 260 mg/ml to 350 mg/ml, 265 mg/ml to 350 mg/ml, 270 mg/ml to 350 mg/ml, 275 mg/ml to 350 mg/ml, 280 mg/ml to 350 mg/ml, 285 mg/ml to 350 mg/ml, 290 mg/ml to 350 mg/ml, 295 mg/ml to 350 mg/ml, 300 mg/ml to 350 mg/ml, 305 mg/ml to 350 mg/ml, 310 mg/ml to 350 mg/ml, 315 mg/ml to 350 mg/ml, 320 mg/ml to 350 mg/ml, 325 mg/ml to 350 mg/ml, 330 mg/ml to 350 mg/ml, 335 mg/ml to 350 mg/ml, 340 mg/ml to 350 mg/ml, 345 mg/ml to 350 mg/ml, 260 mg/ml to 340 mg/ml, 265 mg/ml to 340 mg/ml, 270 mg/ml to 340 mg/ml, 275 mg/ml to 340 mg/ml, 280 mg/ml to 340 mg/ml, 285 mg/ml to 340 mg/ml, 290 mg/ml to 340 mg/ml, 295 mg/ml to 340 mg/ml, 300 mg/ml to 340 mg/ml, 305 mg/ml to 340 mg/ml, 310 mg/ml to 340 mg/ml, 315 mg/ml to 340 mg/ml, 320 mg/ml to 340 mg/ml, 325 mg/ml to 340 mg/ml, 330 mg/ml to 340 mg/ml, 335 mg/ml to 340 mg/ml, 260 mg/ml to 330 mg/ml, 265 mg/ml to 330 mg/ml, 270 mg/ml to 330 mg/ml, 275 mg/ml to 330 mg/ml, 280 mg/ml to 330 mg/ml, 285 mg/ml to 330 mg/ml, 290 mg/ml to 330 mg/ml, 295 mg/ml to 330 mg/ml, 300 mg/ml to 330 mg/ml, 305 mg/ml to 330 mg/ml, 310 mg/ml to 330 mg/ml, 315 mg/ml to 330 mg/ml, 320 mg/ml to 330 mg/ml, 325 mg/ml to 330 mg/ml, 260 mg/ml to 320 mg/ml, 265 mg/ml to 320 mg/ml, 270 mg/ml to 320 mg/ml, 275 mg/ml to 320 mg/ml, 280 mg/ml to 320 mg/ml, 285 mg/ml to 320 mg/ml, 290 mg/ml to 320 mg/ml, 295 mg/ml to 320 mg/ml, 300 mg/ml to 320 mg/ml, 305 mg/ml to 320 mg/ml, 310 mg/ml to 320 mg/ml, 315 mg/ml to 320 mg/ml, 260 mg/ml to 310 mg/ml, 265 mg/ml to 310 mg/ml, 270 mg/ml to 310 mg/ml, 275 mg/ml to 310 mg/ml, 280 mg/ml to 310 mg/ml, 285 mg/ml to 310 mg/ml, 290 mg/ml to 310 mg/ml, 295 mg/ml to 310 mg/ml, 300 mg/ml to 310 mg/ml, 305 mg/ml to 310 mg/ml, 260 mg/ml to 310 mg/ml, 265 mg/ml to 300 mg/ml, 270 mg/ml to 300 mg/ml, 275 mg/ml to 300 mg/ml, 280 mg/ml to 300 mg/ml, 285 mg/ml to 300 mg/ml, 290 mg/ml to 300 mg/ml, 295 mg/ml to 300 mg/ml, 265 mg/ml to 290 mg/ml, 270 mg/ml to 290 mg/ml, 275 mg/ml to 290 mg/ml, 280 mg/ml to 290 mg/ml, 285 mg/ml to 290 mg/ml, 265 mg/ml to 280 mg/ml, 270 mg/ml to 280 mg/ml, 275 mg/ml to 280 mg/ml, or about 265 mg/ml to 270 mg/ml. The medroxyprogesterone acetate ranges disclosed in this paragraph are hereby disclosed in combination with the docusate sodium and/or polyethylene glycol ranges disclosed herein. Thus the medroxyprogesterone acetate ranges disclosed in this paragraph are hereby disclosed in combination with a docusate sodium concentration of about 0.6 mg/ml to about 1.5 mg/ml and optionally a polyethylene glycol concentration of about 10 mg/ml to about 40 mg/ml or about 15 mg/ml to about 30 mg/ml. For the sake of brevity, all of the combinations are not being parsed out.

By way of further example, concentrations of medroxyprogesterone acetate (mg/ml) in the composition can comprise about 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439 or about 440 mg/ml. The medroxyprogesterone acetate concentrations disclosed in this paragraph are hereby disclosed in combination with the docusate sodium and/or polyethylene glycol ranges disclosed herein. Thus the medroxyprogesterone acetate ranges disclosed in this paragraph are hereby disclosed in combination with a docusate sodium concentration of about 0.5 mg/ml to about 3 mg/ml, about 0.5 mg/ml to about 1.0 mg/ml or about 0.5 to 0.7 mg/ml, and optionally a polyethylene glycol concentration of about 10 mg/ml to about 40 mg/ml or about 15 mg/ml to about 30 mg/ml. For the sake of brevity, all of the combinations are not being parsed out.

In other aspects, the concentration of medroxyprogesterone acetate in the compositions can range from about 160 mg/ml to 240 mg/ml. For example, the concentrations can range from about 160 mg/ml to 240 mg/ml, 165 mg/ml to 240 mg/ml, 170 mg/ml to 240 mg/ml, 175 mg/ml to 240 mg/ml, 180 mg/ml to 240 mg/ml, 185 mg/ml to 240 mg/ml, 190 mg/ml to 240 mg/ml, 195 mg/ml to 240 mg/ml, 200 mg/ml to 240 mg/ml, 205 mg/ml to 240 mg/ml, 210 mg/ml to 240 mg/ml, 215 mg/ml to 240 mg/ml, 220 mg/ml to 240 mg/ml, 225 mg/ml to 240 mg/ml, 230 mg/ml to 240 mg/ml, 235 mg/ml to 240 mg/ml, 160 mg/ml to 235 mg/ml, 165 mg/ml to 235 mg/ml, 170 mg/ml to 235 mg/ml, 175 mg/ml to 235 mg/ml, 180 mg/ml to 235 mg/ml, 185 mg/ml to 235 mg/ml, 190 mg/ml to 235 mg/ml, 195 mg/ml to 235 mg/ml, 200 mg/ml to 235 mg/ml, 205 mg/ml to 235 mg/ml, 210 mg/ml to 235 mg/ml, 215 mg/ml to 235 mg/ml, 220 mg/ml to 235 mg/ml, 225 mg/ml to 235 mg/ml, 230 mg/ml to 235 mg/ml, 160 mg/ml to 230 mg/ml, 165 mg/ml to 230 mg/ml, 170 mg/ml to 230 mg/ml, 175 mg/ml to 230 mg/ml, 180 mg/ml to 230 mg/ml, 185 mg/ml to 230 mg/ml, 190 mg/ml to 230 mg/ml, 195 mg/ml to 230 mg/ml, 200 mg/ml to 230 mg/ml, 205 mg/ml to 230 mg/ml, 210 mg/ml to 230 mg/ml, 215 mg/ml to 230 mg/ml, 220 mg/ml to 230 mg/ml, 225 mg/ml to 230 mg/ml, 160 mg/ml to 225 mg/ml, 165 mg/ml to 225 mg/ml, 170 mg/ml to 225 mg/ml, 175 mg/ml to 225 mg/ml, 180 mg/ml to 225 mg/ml, 185 mg/ml to 225 mg/ml, 190 mg/ml to 225 mg/ml, 195 mg/ml to 225 mg/ml, 200 mg/ml to 225 mg/ml, 205 mg/ml to 225 mg/ml, 210 mg/ml to 225 mg/ml, 215 mg/ml to 225 mg/ml, 220 mg/ml to 225 mg/ml, 160 mg/ml to 220 mg/ml, 165 mg/ml to 220 mg/ml, 170 mg/ml to 220 mg/ml, 175 mg/ml to 220 mg/ml, 180 mg/ml to 220 mg/ml, 185 mg/ml to 220 mg/ml, 190 mg/ml to 220 mg/ml, 195 mg/ml to 220 mg/ml, 200 mg/ml to 220 mg/ml, 205 mg/ml to 220 mg/ml, 210 mg/ml to 220 mg/ml, 215 mg/ml to 220 mg/ml, 160 mg/ml to 215 mg/ml, 165 mg/ml to 215 mg/ml, 170 mg/ml to 215 mg/ml, 175 mg/ml to 215 mg/ml, 180 mg/ml to 215 mg/ml, 185 mg/ml to 215 mg/ml, 190 mg/ml to 215 mg/ml, 195 mg/ml to 215 mg/ml, 200 mg/ml to 215 mg/ml, 205 mg/ml to 215 mg/ml, 210 mg/ml to 215 mg/ml, 160 mg/ml to 210 mg/ml, 165 mg/ml to 210 mg/ml, 170 mg/ml to 210 mg/ml, 175 mg/ml to 210 mg/ml, 180 mg/ml to 210 mg/ml, 185 mg/ml to 210 mg/ml, 190 mg/ml to 210 mg/ml, 195 mg/ml to 210 mg/ml, 200 mg/ml to 210 mg/ml, 205 mg/ml to 210 mg/ml, 160 mg/ml to 205 mg/ml, 165 mg/ml to 205 mg/ml, 170 mg/ml to 205 mg/ml, 175 mg/ml to 205 mg/ml, 180 mg/ml to 205 mg/ml, 185 mg/ml to 205 mg/ml, 190 mg/ml to 205 mg/ml, 195 mg/ml to 205 mg/ml, 200 mg/ml to 205 mg/ml, 160 mg/ml to 200 mg/ml, 165 mg/ml to 200 mg/ml, 170 mg/ml to 200 mg/ml, 175 mg/ml to 200 mg/ml, 180 mg/ml to 200 mg/ml, 185 mg/ml to 200 mg/ml, 190 mg/ml to 200 mg/ml, 195 mg/ml to 200 mg/ml, 160 mg/ml to 195 mg/ml, 165 mg/ml to 195 mg/ml, 170 mg/ml to 195 mg/ml, 175 mg/ml to 195 mg/ml, 180 mg/ml to 195 mg/ml, 185 mg/ml to 195 mg/ml, 190 mg/ml to 195 mg/ml, 160 mg/ml to 190 mg/ml, 165 mg/ml to 190 mg/ml, 170 mg/ml to 190 mg/ml, 175 mg/ml to 190 mg/ml, 180 mg/ml to 190 mg/ml, 185 mg/ml to 190 mg/ml, 160 mg/ml to 185 mg/ml, 165 mg/ml to 185 mg/ml, 170 mg/ml to 185 mg/ml, 175 mg/ml to 185 mg/ml, 180 mg/ml to 185 mg/ml, 160 mg/ml to 180 mg/ml, 165 mg/ml to 180 mg/ml, 170 mg/ml to 180 mg/ml, 175 mg/ml to 180 mg/ml, 160 mg/ml to 175 mg/ml, 165 mg/ml to 175 mg/ml, 170 mg/ml to 175 mg/ml, 160 mg/ml to 170 mg/ml, 165 mg/ml to 170 mg/ml, or about 160 mg/ml to 165 mg/ml. The medroxyprogesterone acetate ranges disclosed in this paragraph are hereby disclosed in combination with the docusate sodium and/or polyethylene glycol ranges disclosed herein, preferably in combination with a docusate sodium concentration of about 0.5 mg/ml to about 3 mg/ml or about 0.6 mg/ml to about 1.5 mg/ml and optionally a polyethylene glycol concentration of about 10 mg/ml to about 40 mg/ml or about 15 mg/ml to about 30 mg/ml. For the sake of brevity, all of the combinations are not being parsed out.

By way of further example, concentrations of medroxyprogesterone acetate in the composition can comprise about 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, or about 240 mg/ml. The medroxyprogesterone acetate concentrations disclosed in this paragraph are hereby disclosed in combination with the docusate sodium and/or polyethylene glycol ranges disclosed herein, preferably in combination with a docusate sodium concentration of about 1.2 mg/ml to 3 mg/ml and optionally a polyethylene glycol concentration of about 10 mg/ml to 40 mg/ml. For the sake of brevity, all of the combinations are not being parsed out.

The compositions of the disclosure further comprise docusate sodium. As used herein, "docusate sodium" refers to the excipient with the molecular formula $C_{20}H_{37}NaO_7S$, and may also be referred to by one of skill in the art as dioctyl sodium sulfosuccinate or DSS. The compositions of the disclosure may comprise a concentration of docusate sodium that ranges from about 0.5 mg/ml to about 3.0 mg/ml. In certain embodiments, the concentration of docusate sodium can range from about 0.6 mg/ml to about 1.5 mg/ml. For example, the concentrations can range from about 0.5 mg/ml to 3.0 mg/ml, 0.6 mg/ml to 3.0 mg/ml, 0.7 mg/ml to 3.0 mg/ml, 0.8 mg/ml to 3.0 mg/ml, 0.9 mg/ml to 3.0 mg/ml, 1.0 mg/ml to 3.0 mg/ml, 1.1 mg/ml to 3.0 mg/ml, 1.2 mg/ml to 3.0 mg/ml, 1.3 mg/ml to 3.0 mg/ml, 1.4 mg/ml to 3.0 mg/ml, 1.5 mg/ml to 3.0 mg/ml, 1.6 mg/ml to 3.0 mg/ml, 1.7 mg/ml to 3.0 mg/ml, 1.8 mg/ml to 3.0 mg/ml, 1.9 mg/ml to 3.0 mg/ml, 2.0 mg/ml to 3.0 mg/ml, 2.1 mg/ml to 3.0 mg/ml, 2.2 mg/ml to 3.0 mg/ml, 2.3 mg/ml to 3.0 mg/ml, 2.4 mg/ml to 3.0 mg/ml, 2.5 mg/ml to 3.0 mg/ml, 2.6 mg/ml to 3.0 mg/ml, 2.7 mg/ml to 3.0 mg/ml, 2.8 mg/ml to 3.0 mg/ml, 2.9 mg/ml to 3.0 mg/ml, 0.5 mg/ml to 2.9 mg/ml, 0.6 mg/ml to 2.9 mg/ml, 0.7 mg/ml to 2.9 mg/ml, 0.8 mg/ml to 2.9 mg/ml, 0.9 mg/ml to 2.9 mg/ml, 1.0 mg/ml to 2.9 mg/ml, 1.1 mg/ml to 2.9 mg/ml, 1.2 mg/ml to 2.9 mg/ml, 1.3 mg/ml to 2.9 mg/ml, 1.4 mg/ml to 2.9 mg/ml, 1.5 mg/ml to 2.9 mg/ml, 1.6 mg/ml to 2.9 mg/ml, 1.7 mg/ml to 2.9 mg/ml, 1.8 mg/ml to 2.9 mg/ml, 1.9 mg/ml to 2.9 mg/ml, 2.0 mg/ml to 2.9 mg/ml, 2.1 mg/ml to 2.9 mg/ml, 2.2 mg/ml to 2.9 mg/ml, 2.3 mg/ml to 2.9 mg/ml, 2.4 mg/ml to 2.9 mg/ml, 2.5 mg/ml to 2.9 mg/ml, 2.6 mg/ml to 2.9 mg/ml, 2.7 mg/ml to 2.9 mg/ml, 2.8 mg/ml to 2.9 mg/ml, 0.5 mg/ml to 2.8 mg/ml, 0.6 mg/ml to 2.8 mg/ml, 0.7 mg/ml to 2.8 mg/ml, 0.8 mg/ml to 2.8 mg/ml, 0.9 mg/ml to 2.8 mg/ml, 1.0 mg/ml to 2.8 mg/ml, 1.1 mg/ml to 2.8 mg/ml, 1.2 mg/ml to 2.8 mg/ml, 1.3 mg/ml to 2.8 mg/ml, 1.4 mg/ml to 2.8 mg/ml, 1.5 mg/ml to 2.8 mg/ml, 1.6 mg/ml to 2.8 mg/ml, 1.7 mg/ml to 2.8 mg/ml, 1.8 mg/ml to 2.8 mg/ml, 1.9 mg/ml to 2.8 mg/ml, 2.0 mg/ml to 2.8 mg/ml, 2.1 mg/ml to 2.8 mg/ml, 2.2 mg/ml to 2.8 mg/ml, 2.3 mg/ml to 2.8 mg/ml, 2.4 mg/ml to 2.8 mg/ml, 2.5 mg/ml to 2.8 mg/ml, 2.6 mg/ml to 2.8 mg/ml, 2.7 mg/ml to 2.8 mg/ml, 0.5 mg/ml to 2.7 mg/ml, 0.6 mg/ml to 2.7 mg/ml, 0.7 mg/ml to 2.7 mg/ml, 0.8 mg/ml to 2.7 mg/ml, 0.9 mg/ml to 2.7 mg/ml, 1.0 mg/ml to 2.7 mg/ml, 1.1 mg/ml to 2.7 mg/ml, 1.2 mg/ml to 2.7 mg/ml, 1.3 mg/ml to 2.7 mg/ml, 1.4 mg/ml to 2.7 mg/ml, 1.5 mg/ml to 2.7 mg/ml, 1.6 mg/ml to 2.7 mg/ml, 1.7 mg/ml to 2.7 mg/ml, 1.8 mg/ml to 2.7 mg/ml, 1.9 mg/ml to 2.7 mg/ml, 2.0 mg/ml to 2.7 mg/ml, 2.1 mg/ml to 2.7 mg/ml, 2.2 mg/ml to 2.7 mg/ml, 2.3 mg/ml to 2.7 mg/ml, 2.4 mg/ml to 2.7 mg/ml, 2.5 mg/ml to 2.7 mg/ml, 2.6 mg/ml to 2.7 mg/ml, 0.5 mg/ml to 2.6 mg/ml, 0.6 mg/ml to 2.6 mg/ml, 0.7 mg/ml to 2.6 mg/ml, 0.8 mg/ml to 2.6 mg/ml, 0.9 mg/ml to 2.6 mg/ml, 1.0 mg/ml to 2.6 mg/ml, 1.1 mg/ml to 2.6 mg/ml, 1.2 mg/ml to 2.6 mg/ml, 1.3 mg/ml to 2.6 mg/ml, 1.4 mg/ml to 2.6 mg/ml, 1.5 mg/ml to 2.6 mg/ml, 1.6 mg/ml to 2.6 mg/ml, 1.7 mg/ml to 2.6 mg/ml, 1.8 mg/ml to 2.6 mg/ml, 1.9 mg/ml to 2.6 mg/ml, 2.0 mg/ml to 2.6 mg/ml, 2.1 mg/ml to 2.6 mg/ml, 2.2 mg/ml to 2.6 mg/ml, 2.3 mg/ml to 2.6 mg/ml, 2.4 mg/ml to 2.6 mg/ml, 2.5 mg/ml to 2.6 mg/ml, 0.5 mg/ml to 2.9 mg/ml, 0.6 mg/ml to 2.5 mg/ml, 0.7 mg/ml to 2.5 mg/ml, 0.8 mg/ml to 2.5 mg/ml, 0.9 mg/ml to 2.5 mg/ml, 1.0 mg/ml to 2.5 mg/ml, 1.1 mg/ml to 2.5 mg/ml, 1.2 mg/ml to 2.5 mg/ml, 1.3 mg/ml to 2.5 mg/ml, 1.4 mg/ml to 2.5 mg/ml, 1.5 mg/ml to 2.5 mg/ml, 1.6 mg/ml to 2.5 mg/ml, 1.7 mg/ml to 2.5 mg/ml, 1.8 mg/ml to 2.5 mg/ml, 1.9 mg/ml to 2.5 mg/ml, 2.0 mg/ml to 2.5 mg/ml, 2.1 mg/ml to 2.5 mg/ml, 2.2 mg/ml to 2.5 mg/ml, 2.3 mg/ml to 2.5 mg/ml, 2.4 mg/ml to 2.5 mg/ml, 0.5 mg/ml to 2.4 mg/ml, 0.6 mg/ml to 2.4 mg/ml, 0.7 mg/ml to 2.4 mg/ml, 0.8 mg/ml to 2.4 mg/ml, 0.9 mg/ml to 2.4 mg/ml, 1.0 mg/ml to 2.4 mg/ml, 1.1 mg/ml to 2.4 mg/ml, 1.2 mg/ml to 2.4 mg/ml, 1.3 mg/ml to 2.4 mg/ml, 1.4 mg/ml to 2.4 mg/ml, 1.5 mg/ml to 2.4 mg/ml, 1.6 mg/ml to 2.4 mg/ml, 1.7 mg/ml to 2.4 mg/ml, 1.8 mg/ml to 2.4 mg/ml, 1.9 mg/ml to 2.4 mg/ml, 2.0 mg/ml to 2.4 mg/ml, 2.1 mg/ml to 2.4 mg/ml, 2.2 mg/ml to 2.4 mg/ml, 2.3 mg/ml to 2.4 mg/ml, 0.5 mg/ml to 2.3 mg/ml, 0.6 mg/ml to 2.3 mg/ml, 0.7 mg/ml to 2.3 mg/ml, 0.8 mg/ml to 2.3 mg/ml, 0.9 mg/ml to 2.3 mg/ml, 1.0 mg/ml to 2.3 mg/ml, 1.1 mg/ml to 2.3 mg/ml, 1.2 mg/ml to 2.3 mg/ml, 1.3 mg/ml to 2.3 mg/ml, 1.4 mg/ml to 2.3 mg/ml, 1.5 mg/ml to 2.3 mg/ml, 1.6 mg/ml to 2.3 mg/ml, 1.7 mg/ml to 2.3 mg/ml, 1.8 mg/ml to 2.3 mg/ml, 1.9 mg/ml to 2.3 mg/ml, 2.0 mg/ml to 2.3 mg/ml, 2.1 mg/ml to 2.3 mg/ml, 2.2 mg/ml to 2.3 mg/ml, 0.5 mg/ml to 2.2 mg/ml, 0.6 mg/ml to 2.2 mg/ml, 0.7 mg/ml to 2.2 mg/ml, 0.8 mg/ml to 2.2 mg/ml, 0.9 mg/ml to 2.2 mg/ml, 1.0 mg/ml to 2.2 mg/ml, 1.1 mg/ml to 2.2 mg/ml, 1.2 mg/ml to 2.2 mg/ml, 1.3 mg/ml to 2.2 mg/ml, 1.4 mg/ml to 2.2 mg/ml, 1.5 mg/ml to 2.2 mg/ml, 1.6 mg/ml to 2.2 mg/ml, 1.7 mg/ml to 2.2 mg/ml, 1.8 mg/ml to 2.2 mg/ml, 1.9 mg/ml to 2.2 mg/ml, 2.0 mg/ml to 2.2 mg/ml, 2.1 mg/ml to 2.2 mg/ml, 0.5 mg/ml to 2.1 mg/ml, 0.6 mg/ml to 2.1 mg/ml, 0.7 mg/ml to 2.1 mg/ml, 0.8 mg/ml to 2.1 mg/ml, 0.9 mg/ml to 2.1 mg/ml, 1.0 mg/ml to 2.1 mg/ml, 1.1 mg/ml to 2.1 mg/ml, 1.2 mg/ml to 2.1 mg/ml, 1.3 mg/ml to 2.1 mg/ml, 1.4 mg/ml to 2.1 mg/ml, 1.5 mg/ml to 2.1 mg/ml, 1.6 mg/ml to 2.1 mg/ml, 1.7 mg/ml to 2.1 mg/ml, 1.8 mg/ml to 2.1 mg/ml, 1.9 mg/ml to 2.1 mg/ml, 2.0 mg/ml to 2.1 mg/ml, 0.5 mg/ml to 2.0 mg/ml, 0.6 mg/ml to 2.0 mg/ml, 0.7 mg/ml to 2.0 mg/ml, 0.8 mg/ml to 2.0 mg/ml, 0.9 mg/ml to 2.0 mg/ml, 1.0 mg/ml to 2.0 mg/ml, 1.1 mg/ml to 2.0 mg/ml, 1.2 mg/ml to 2.0 mg/ml, 1.3 mg/ml to 2.0 mg/ml, 1.4 mg/ml to 2.0 mg/ml, 1.5 mg/ml to 2.0 mg/ml, 1.6 mg/ml to 2.0 mg/ml, 1.7 mg/ml to 2.0 mg/ml, 1.8 mg/ml to 2.0 mg/ml, 1.9 mg/ml to 2.0 mg/ml, 0.5 mg/ml to 1.9 mg/ml, 0.6 mg/ml to 1.9 mg/ml, 0.7 mg/ml to 1.9 mg/ml, 0.8 mg/ml to 1.9 mg/ml, 0.9 mg/ml to 1.9 mg/ml, 1.0 mg/ml to 1.9 mg/ml, 1.1 mg/ml to 1.9 mg/ml, 1.2 mg/ml to 1.9 mg/ml, 1.3 mg/ml to 1.9 mg/ml, 1.4 mg/ml to 1.9 mg/ml, 1.5 mg/ml to 1.9 mg/ml, 1.6 mg/ml to 1.9 mg/ml, 1.7 mg/ml to 1.9 mg/ml, 1.8 mg/ml to 1.9 mg/ml, 0.5 mg/ml to 1.8 mg/ml, 0.6 mg/ml to 1.8 mg/ml, 0.7 mg/ml to 1.8 mg/ml, 0.8 mg/ml to 1.8 mg/ml, 0.9 mg/ml to 1.8 mg/ml, 1.0 mg/ml to 1.8 mg/ml, 1.1 mg/ml to 1.8 mg/ml, 1.2 mg/ml to 1.8 mg/ml, 1.3 mg/ml to 1.8 mg/ml, 1.4 mg/ml to 1.8 mg/ml, 1.5 mg/ml to 1.8 mg/ml, 1.6 mg/ml to 1.8 mg/ml, 1.7 mg/ml to 1.8 mg/ml, 0.5 mg/ml to 1.7 mg/ml, 0.6 mg/ml to 1.7 mg/ml, 0.7 mg/ml to 1.7 mg/ml, 0.8 mg/ml to 1.7 mg/ml, 0.9 mg/ml to 1.7 mg/ml, 1.0 mg/ml to 1.7 mg/ml, 1.1 mg/ml to 1.7 mg/ml, 1.2 mg/ml to 1.7 mg/ml, 1.3 mg/ml to 1.7 mg/ml, 1.4 mg/ml to 1.7 mg/ml, 1.5 mg/ml to 1.7 mg/ml, 1.6 mg/ml to 1.7 mg/ml, 0.5 mg/ml to 1.6 mg/ml, 0.6 mg/ml to 1.6 mg/ml, 0.7 mg/ml to 1.6 mg/ml, 0.8 mg/ml to 1.6 mg/ml, 0.9 mg/ml to 1.6 mg/ml, 1.0 mg/ml to 1.6 mg/ml, 1.1 mg/ml to 1.6 mg/ml, 1.2 mg/ml to 1.6 mg/ml, 1.3 mg/ml to 1.6 mg/ml, 1.4 mg/ml to 1.6 mg/ml, 1.5 mg/ml to 1.6 mg/ml, 0.5 mg/ml to 1.5 mg/ml, 0.6 mg/ml to 1.5 mg/ml, 0.7 mg/ml to 1.5 mg/ml, 0.8 mg/ml to 1.5 mg/ml, 0.9 mg/ml to 1.5 mg/ml, 1.0 mg/ml to 1.5 mg/ml, 1.1 mg/ml to 1.5 mg/ml, 1.2 mg/ml to 1.5 mg/ml, 1.3 mg/ml to 1.5 mg/ml, 1.4 mg/ml to 1.5 mg/ml, 0.5 mg/ml to 1.4 mg/ml, 0.6 mg/ml to 1.4 mg/ml, 0.7 mg/ml to 1.4 mg/ml, 0.8 mg/ml to 1.4 mg/ml, 0.9 mg/ml to 1.4 mg/ml, 1.0 mg/ml to 1.4 mg/ml, 1.1 mg/ml to 1.4 mg/ml, 1.2 mg/ml to 1.4 mg/ml, 1.3 mg/ml to 1.4 mg/ml, 0.5 mg/ml to 1.3 mg/ml, 0.6 mg/ml to 1.3 mg/ml, 0.7 mg/ml to 1.3 mg/ml, 0.8 mg/ml to 1.3 mg/ml, 0.9 mg/ml to 1.3 mg/ml, 1.0 mg/ml to 1.3 mg/ml, 1.1 mg/ml to 1.3 mg/ml, 1.2 mg/ml to 1.3 mg/ml, 0.5 mg/ml to 1.2 mg/ml, 0.6 mg/ml to 1.2 mg/ml, 0.7 mg/ml to 1.2 mg/ml, 0.8 mg/ml to 1.2 mg/ml, 0.9 mg/ml to 1.2 mg/ml, 1.0 mg/ml to 1.2 mg/ml, 1.1 mg/ml to 1.2 mg/ml, 0.5 mg/ml to 1.1 mg/ml, 0.6 mg/ml to 1.1 mg/ml, 0.7 mg/ml to 1.1 mg/ml, 0.8 mg/ml to 1.1 mg/ml, 0.9 mg/ml to 1.1 mg/ml, 1.0 mg/ml to 1.1 mg/ml, 0.5 mg/ml to 1.0 mg/ml, 0.6 mg/ml to 1.0 mg/ml, 0.7 mg/ml to 1.0 mg/ml, 0.8 mg/ml to 1.0 mg/ml, 0.9 mg/ml to 1.0 mg/ml, 1.0 mg/ml to 1.0 mg/ml, 0.5 mg/ml to 0.9 mg/ml, 0.6 mg/ml to 0.9 mg/ml, 0.7 mg/ml to 0.9 mg/ml, 0.8 mg/ml to 0.9 mg/ml, 0.5 mg/ml to 0.8 mg/ml, 0.6 mg/ml to 0.8 mg/ml, 0.7 mg/ml to 0.8 mg/ml, 0.5 mg/ml to 0.7 mg/ml, or about 0.6 mg/ml to 0.7 mg/ml, The docusate sodium ranges disclosed in this paragraph are hereby disclosed in combination with the medroxyprogesterone and polyethylene glycol ranges disclosed herein. Thus the docusate sodium ranges disclosed in this paragraph are hereby disclosed in combination with a medroxyprogesterone concentration of about 260 mg/ml to 440 mg/ml, 260 mg/ml to 340 mg/ml, 270 mg/ml to 330 mg/ml, 280 mg/ml to 320 mg/ml, 290 mg/ml to 310 mg/ml, 295 mg/ml to 305 mg/ml, 370 mg/ml to 430 mg/ml, 380 mg/ml to 420 mg/ml, 390 mg/ml to 410 mg/ml, or 395 mg/ml to 405 mg/ml, and optionally a polyethylene glycol concentration of about 10 mg/ml to about 40 mg/ml. For the sake of brevity, all of the combinations are not being parsed out.

By way of further example, concentrations of docusate sodium can comprise about 0.5, 0.6, 0.7, 0.8, 0.9, 1.0, 1.1 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or about 3.0 mg/ml. The docusate sodium concentrations disclosed in this paragraph are hereby disclosed in combination with the medroxyprogesterone and/or polyethylene glycol ranges disclosed herein. Thus the docusate sodium ranges disclosed in this paragraph are hereby disclosed in combination with a medroxyprogesterone concentration of about 260 mg/ml to 440 mg/ml, 260 mg/ml to 340 mg/ml, 270 mg/ml to 330 mg/ml, 280 mg/ml to 320 mg/ml, 290 mg/ml to 310 mg/ml, 295 mg/ml to 305 mg/ml, 370 mg/ml to 430 mg/ml, 380 mg/ml to 420 mg/ml, 390 mg/ml to 410 mg/ml, or 395 mg/ml to 405 mg/ml, and optionally a polyethylene glycol concentration of about 10 mg/ml to about 40 mg/ml. For the sake of brevity, all of the combinations are not being parsed out.

In preferred aspects, the compositions described herein comprise medroxyprogesterone acetate at a concentration of about 260 mg/ml to about 340 mg/ml and docusate sodium at a concentration of about 0.5 mg/ml to about 3.0 mg/ml. In further preferred aspects, the compositions described herein comprise medroxyprogesterone acetate at a concentration of about 260 mg/ml to about 340 mg/ml and docusate sodium at a concentration of about 0.5 mg/ml to about 1.0 mg/ml. In still further preferred aspects, the compositions described herein comprise medroxyprogesterone acetate at a concentration of about 260 mg/ml to about 340 mg/ml and docusate sodium at a concentration of about 0.5 mg/ml to about 0.7 mg/ml.

In other preferred aspects, the compositions described herein comprise medroxyprogesterone acetate at a concentration of about 270 mg/ml to about 330 mg/ml and docusate sodium at a concentration of about 0.5 mg/ml to about 3.0 mg/ml. In further preferred aspects, the compositions described herein comprise medroxyprogesterone acetate at a concentration of about 270 mg/ml to about 330 mg/ml and docusate sodium at a concentration of about 0.5 mg/ml to about 1.0 mg/ml. In still further preferred aspects, the compositions described herein comprise medroxyprogesterone acetate at a concentration of about 270 mg/ml to about 330 mg/ml and docusate sodium at a concentration of about 0.5 mg/ml to about 0.7 mg/ml.

In still other preferred aspects, the compositions described herein comprise medroxyprogesterone acetate at a concentration of about 280 mg/ml to about 320 mg/ml and docusate sodium at a concentration of about 0.5 mg/ml to about 3.0 mg/ml. In further preferred aspects, the compositions described herein comprise medroxyprogesterone acetate at a concentration of about 280 mg/ml to about 320 mg/ml and docusate sodium at a concentration of about 0.5 mg/ml to about 1.0 mg/ml. In still further preferred aspects, the compositions described herein comprise medroxyprogesterone acetate at a concentration of about 280 mg/ml to about 320 mg/ml and docusate sodium at a concentration of about 0.5 mg/ml to about 0.7 mg/ml.

In further preferred aspects, the compositions described herein comprise medroxyprogesterone acetate at a concentration of about 290 mg/ml to about 310 mg/ml and docusate sodium at a concentration of about 0.5 mg/ml to about 3.0 mg/ml. In further preferred aspects, the compositions described herein comprise medroxyprogesterone acetate at a concentration of about 290 mg/ml to about 310 mg/ml and docusate sodium at a concentration of about 0.5 mg/ml to about 1.0 mg/ml. In still further preferred aspects, the compositions described herein comprise medroxyprogesterone acetate at a concentration of about 290 mg/ml to about 310 mg/ml and docusate sodium at a concentration of about 0.5 mg/ml to about 0.7 mg/ml.

In still further preferred aspects, the compositions described herein comprise medroxyprogesterone acetate at a concentration of about 295 mg/ml to about 305 mg/ml and docusate sodium at a concentration of about 0.5 mg/ml to about 3.0 mg/ml. In further preferred aspects, the compositions described herein comprise medroxyprogesterone acetate at a concentration of about 295 mg/ml to about 305 mg/ml and docusate sodium at a concentration of about 0.5 mg/ml to about 1.0 mg/ml. In still further preferred aspects, the compositions described herein comprise medroxyprogesterone acetate at a concentration of about 295 mg/ml to about 305 mg/ml and docusate sodium at a concentration of about 0.5 mg/ml to about 0.7 mg/ml.

In preferred aspects, the compositions described herein comprise medroxyprogesterone acetate at a concentration of about 360 mg/ml to about 440 mg/ml and docusate sodium at a concentration of about 0.5 mg/ml to about 3.0 mg/ml. In further preferred aspects, the compositions described herein comprise medroxyprogesterone acetate at a concentration of about 360 mg/ml to about 440 mg/ml and docusate sodium at a concentration of about 0.5 mg/ml to about 1.0 mg/ml. In still further preferred aspects, the compositions described herein comprise medroxyprogesterone acetate at a concentration of about 360 mg/ml to about 440 mg/ml and docusate sodium at a concentration of about 0.5 mg/ml to about 0.7 mg/ml.

In other preferred aspects, the compositions described herein comprise medroxyprogesterone acetate at a concentration of about 370 mg/ml to about 430 mg/ml and docusate sodium at a concentration of about 0.5 mg/ml to about 3.0 mg/ml. In further preferred aspects, the compositions described herein comprise medroxyprogesterone acetate at a concentration of about 370 mg/ml to about 430 mg/ml and docusate sodium at a concentration of about 0.5 mg/ml to about 1.0 mg/ml. In still further preferred aspects, the compositions described herein comprise medroxyprogesterone acetate at a concentration of 370 mg/ml to about 430 mg/ml and docusate sodium at a concentration of about 0.5 mg/ml to about 0.7 mg/ml.

In still other preferred aspects, the compositions described herein comprise medroxyprogesterone acetate at a concentration of about 380 mg/ml to about 420 mg/ml and docusate sodium at a concentration of about 0.5 mg/ml to about 3.0 mg/ml. In further preferred aspects, the compositions described herein comprise medroxyprogesterone acetate at a concentration of about 380 mg/ml to about 420 mg/ml mg/ml and docusate sodium at a concentration of about 0.5 mg/ml to about 1.0 mg/ml. In still further preferred aspects, the compositions described herein comprise medroxyprogesterone acetate at a concentration of about 380 mg/ml to about 420 mg/ml mg/ml and docusate sodium at a concentration of about 0.5 mg/ml to about 0.7 mg/ml.

In further preferred aspects, the compositions described herein comprise medroxyprogesterone acetate at a concentration of about 390 mg/ml to about 410 mg/ml and docusate sodium at a concentration of about 0.5 mg/ml to about 3.0 mg/ml. In further preferred aspects, the compositions described herein comprise medroxyprogesterone acetate at a concentration of about 390 mg/ml to about 410 mg/ml and docusate sodium at a concentration of about 0.5 mg/ml to about 1.0 mg/ml. In still further preferred aspects, the compositions described herein comprise medroxyprogesterone acetate at a concentration of about 390 mg/ml to about 410 mg/ml and docusate sodium at a concentration of about 0.5 mg/ml to about 0.7 mg/ml.

In still further preferred aspects, the compositions described herein comprise medroxyprogesterone acetate at a concentration of about 395 mg/ml to about 405 mg/ml and docusate sodium at a concentration of about 0.5 mg/ml to about 3.0 mg/ml. In further preferred aspects, the compositions described herein comprise medroxyprogesterone acetate at a concentration of about 395 mg/ml to about 405 mg/ml and docusate sodium at a concentration of about 0.5 mg/ml to about 1.0 mg/ml. In still further preferred aspects, the compositions described herein comprise medroxyprogesterone acetate at a concentration of about 395 mg/ml to about 405 mg/ml mg/ml and docusate sodium at a concentration of about 0.5 mg/ml to about 0.7 mg/ml. By way of further example, the compositions described herein comprise medroxyprogesterone acetate at a concentration of about 300 mg/ml to about 400 mg/ml and docusate sodium at a concentration of about 0.6 mg/ml to about 1.3 mg/ml.

The compositions of the disclosure further comprise polyethylene glycol. Polyethylene glycol, or PEG, is a polyether compound that may also be referred to by one of skill in the art as polyethylene oxide or polyoxyethylene, depending on its molecular weight. In preferred embodiments, polyethylene glycol has an average molecular weight of between about 3,000 and about 3,700 g/mol. Most preferably, polyethylene glycol has an average molecular weight of about 3,350 g/mol. Concentrations of polyethylene glycol in the compositions of the disclosure preferably range from about 10 mg/ml to about 40 mg/ml. For example, concentrations may range from about 10 mg/ml to 40 mg/ml, 11 mg/ml to 40 mg/ml, 12 mg/ml to 40 mg/ml, 13 mg/ml to 40 mg/ml, 14 mg/ml to 40 mg/ml, 15 mg/ml to 40 mg/ml, 16 mg/ml to 40 mg/ml, 17 mg/ml to 40 mg/ml, 18 mg/ml to 40 mg/ml, 19 mg/ml to 40 mg/ml, 20 mg/ml to 40 mg/ml, 21 mg/ml to 40 mg/ml, 22 mg/ml to 40 mg/ml, 23 mg/ml to 40 mg/ml, 24 mg/ml to 40 mg/ml, 25 mg/ml to 40 mg/ml, 26 mg/ml to 40 mg/ml, 27 mg/ml to 40 mg/ml, 28 mg/ml to 40 mg/ml, 29 mg/ml to 40 mg/ml, 30 mg/ml to 40 mg/ml, 30 mg/ml to 40 mg/ml, 31 mg/ml to 40 mg/ml, 32 mg/ml to 40 mg/ml, 33 mg/ml to 40 mg/ml, 34 mg/ml to 40 mg/ml, 35 mg/ml to 40 mg/ml, 36 mg/ml to 40 mg/ml, 37 mg/ml to 40 mg/ml, 38 mg/ml to 40 mg/ml, 39 mg/ml to 40 mg/ml, 10 mg/ml to 39 mg/ml, 11 mg/ml to 39 mg/ml, 12 mg/ml to 39 mg/ml, 13 mg/ml to 39 mg/ml, 14 mg/ml to 39 mg/ml, 15 mg/ml to 39 mg/ml, 16 mg/ml to 39 mg/ml, 17 mg/ml to 39 mg/ml, 18 mg/ml to 39 mg/ml, 19 mg/ml to 39 mg/ml, 20 mg/ml to 39 mg/ml, 21 mg/ml to 39 mg/ml, 22 mg/ml to 39 mg/ml, 23 mg/ml to 39 mg/ml, 24 mg/ml to 39 mg/ml, 25 mg/ml to 39 mg/ml, 26 mg/ml to 39 mg/ml, 27 mg/ml to 39 mg/ml, 28 mg/ml to 39 mg/ml, 29 mg/ml to 39 mg/ml, 30 mg/ml to 39 mg/ml, 30 mg/ml to 39 mg/ml, 31 mg/ml to 39 mg/ml, 32 mg/ml to 39 mg/ml, 33 mg/ml to 39 mg/ml, 34 mg/ml to 39 mg/ml, 35 mg/ml to 39 mg/ml, 36 mg/ml to 39 mg/ml, 37 mg/ml to 39 mg/ml, 38 mg/ml to 39 mg/ml, 10 mg/ml to 38 mg/ml, 11 mg/ml to 38 mg/ml, 12 mg/ml to 38 mg/ml, 13 mg/ml to 38 mg/ml, 14 mg/ml to 38 mg/ml, 15 mg/ml to 38 mg/ml, 16 mg/ml to 38 mg/ml, 17 mg/ml to 38 mg/ml, 18 mg/ml to 38 mg/ml, 19 mg/ml to 38 mg/ml, 20 mg/ml to 38 mg/ml, 21 mg/ml to 38 mg/ml, 22 mg/ml to 38 mg/ml, 23 mg/ml to 38 mg/ml, 24 mg/ml to 38 mg/ml, 25 mg/ml to 38 mg/ml, 26 mg/ml to 38 mg/ml, 27 mg/ml to 38 mg/ml, 28 mg/ml to 38 mg/ml, 29 mg/ml to 38 mg/ml, 30 mg/ml to 38 mg/ml, 30 mg/ml to 38 mg/ml, 31 mg/ml to 38 mg/ml, 32 mg/ml to 38 mg/ml, 33 mg/ml to 38 mg/ml, 34 mg/ml to 38 mg/ml, 35 mg/ml to 38 mg/ml, 36 mg/ml to 38 mg/ml, 37 mg/ml to 38 mg/ml, 10 mg/ml to 37 mg/ml, 11 mg/ml to 37 mg/ml, 12 mg/ml to 37 mg/ml, 13 mg/ml to 37 mg/ml, 14 mg/ml to 37 mg/ml, 15 mg/ml to 37 mg/ml, 16 mg/ml to 37 mg/ml, 17 mg/ml to 37 mg/ml, 18 mg/ml to 37 mg/ml, 19 mg/ml to 37 mg/ml, 20 mg/ml to 37 mg/ml, 21 mg/ml to 37 mg/ml, 22 mg/ml to 37 mg/ml, 23 mg/ml to 37 mg/ml, 24 mg/ml to 37 mg/ml, 25 mg/ml to 37 mg/ml, 26 mg/ml to 37 mg/ml, 27 mg/ml to 37 mg/ml, 28 mg/ml to 37 mg/ml, 29 mg/ml to 37 mg/ml, 30 mg/ml to 37 mg/ml, 30 mg/ml to 37 mg/ml, 31 mg/ml to 37 mg/ml, 32 mg/ml to 37 mg/ml, 33 mg/ml to 37 mg/ml, 34 mg/ml to 37 mg/ml, 35 mg/ml to 37 mg/ml, 36 mg/ml to 37 mg/ml, 10 mg/ml to 36 mg/ml, 11 mg/ml to 36 mg/ml, 12 mg/ml to 36 mg/ml, 13 mg/ml to 36 mg/ml, 14 mg/ml to 36 mg/ml, 15 mg/ml to 36 mg/ml, 16 mg/ml to 36 mg/ml, 17 mg/ml to 36 mg/ml, 18 mg/ml to 36 mg/ml, 19 mg/ml to 36 mg/ml, 20 mg/ml to 36 mg/ml, 21 mg/ml to 36 mg/ml, 22 mg/ml to 36 mg/ml, 23 mg/ml to 36 mg/ml, 24 mg/ml to 36 mg/ml, 25 mg/ml to 36 mg/ml, 26 mg/ml to 36 mg/ml, 27 mg/ml to 36 mg/ml, 28 mg/ml to 36 mg/ml, 29 mg/ml to 36 mg/ml, 30 mg/ml to 36 mg/ml, 30 mg/ml to 36 mg/ml, 31 mg/ml to 36 mg/ml, 32 mg/ml to 36 mg/ml, 33 mg/ml to 36 mg/ml, 34 mg/ml to 36 mg/ml, 35 mg/ml to 36 mg/ml, 10 mg/ml to 35 mg/ml, 11 mg/ml to 35 mg/ml, 12 mg/ml to 35 mg/ml, 13 mg/ml to 35 mg/ml, 14 mg/ml to 35 mg/ml, 15 mg/ml to 35 mg/ml, 16 mg/ml to 35 mg/ml, 17 mg/ml to 35 mg/ml, 18 mg/ml to 35 mg/ml, 19 mg/ml to 35 mg/ml, 20 mg/ml to 35 mg/ml, 21 mg/ml to 35 mg/ml, 22 mg/ml to 35 mg/ml, 23 mg/ml to 35 mg/ml, 24 mg/ml to 35 mg/ml, 25 mg/ml to 35 mg/ml, 26 mg/ml to 35 mg/ml, 27 mg/ml to 35 mg/ml, 28 mg/ml to 35 mg/ml, 29 mg/ml to 35 mg/ml, 30 mg/ml to 35 mg/ml, 30 mg/ml to 35 mg/ml, 31 mg/ml to 35 mg/ml, 32 mg/ml to 35 mg/ml, 33 mg/ml to 35 mg/ml, 34 mg/ml to 35 mg/ml, 10 mg/ml to 34 mg/ml, 11 mg/ml to 34 mg/ml, 12 mg/ml to 34 mg/ml, 13 mg/ml to 34 mg/ml, 14 mg/ml to 34 mg/ml, 15 mg/ml to 34 mg/ml, 16 mg/ml to 34 mg/ml, 17 mg/ml to 34 mg/ml, 18 mg/ml to 34 mg/ml, 19 mg/ml to 34 mg/ml, 20 mg/ml to 34 mg/ml, 21 mg/ml to 34 mg/ml, 22 mg/ml to 34 mg/ml, 23 mg/ml to 34 mg/ml, 24 mg/ml to 34 mg/ml, 25 mg/ml to 34 mg/ml, 26 mg/ml to 34 mg/ml, 27 mg/ml to 34 mg/ml, 28 mg/ml to 34 mg/ml, 29 mg/ml to 34 mg/ml, 30 mg/ml to 34 mg/ml, 30 mg/ml to 34 mg/ml, 31 mg/ml to 34 mg/ml, 32 mg/ml to 34 mg/ml, 33 mg/ml to 34 mg/ml, 10 mg/ml to 33 mg/ml, 11 mg/ml to 33 mg/ml, 12 mg/ml to 33 mg/ml, 13 mg/ml to 33 mg/ml, 14 mg/ml to 33 mg/ml, 15 mg/ml to 33 mg/ml, 16 mg/ml to 33 mg/ml, 17 mg/ml to 33 mg/ml, 18 mg/ml to 33 mg/ml, 19 mg/ml to 33 mg/ml, 20 mg/ml to 33 mg/ml, 21 mg/ml to 33 mg/ml, 22 mg/ml to 33 mg/ml, 23 mg/ml to 33 mg/ml, 24 mg/ml to 33 mg/ml, 25 mg/ml to 33 mg/ml, 26 mg/ml to 33 mg/ml, 27 mg/ml to 33 mg/ml, 28 mg/ml to 33 mg/ml, 29 mg/ml to 33 mg/ml, 30 mg/ml to 33 mg/ml, 30 mg/ml to 33 mg/ml, 31 mg/ml to 33 mg/ml, 32 mg/ml to 33 mg/ml, 10 mg/ml to 32 mg/ml, 11 mg/ml to 32 mg/ml, 12 mg/ml to 32 mg/ml, 13 mg/ml to 32 mg/ml, 14 mg/ml to 32 mg/ml, 15 mg/ml to 32 mg/ml, 16 mg/ml to 32 mg/ml, 17 mg/ml to 32 mg/ml, 18 mg/ml to 32 mg/ml, 19 mg/ml to 32 mg/ml, 20 mg/ml to 32 mg/ml, 21 mg/ml to 32 mg/ml, 22 mg/ml to 32 mg/ml, 23 mg/ml to 32 mg/ml, 24 mg/ml to 32 mg/ml, 25 mg/ml to 32 mg/ml, 26 mg/ml to 32 mg/ml, 27 mg/ml to 32 mg/ml, 28 mg/ml to 32 mg/ml, 29 mg/ml to 32 mg/ml, 30 mg/ml to 32 mg/ml, 30 mg/ml to 32 mg/ml, 31 mg/ml to 32 mg/ml, 10 mg/ml to 31 mg/ml, 11 mg/ml to 31 mg/ml, 12 mg/ml to 31 mg/ml, 13 mg/ml to 31 mg/ml, 14 mg/ml to 31 mg/ml, 15 mg/ml to 31 mg/ml, 16 mg/ml to 31 mg/ml, 17 mg/ml to 31 mg/ml, 18 mg/ml to 31 mg/ml, 19 mg/ml to 31 mg/ml, 20 mg/ml to 31 mg/ml, 21 mg/ml to 31 mg/ml, 22 mg/ml to 31 mg/ml, 23 mg/ml to 31 mg/ml, 24 mg/ml to 31 mg/ml, 25 mg/ml to 31 mg/ml, 26 mg/ml to 31 mg/ml, 27 mg/ml to 31 mg/ml, 28 mg/ml to 31 mg/ml, 29 mg/ml to 31 mg/ml, 30 mg/ml to 31 mg/ml, 10 mg/ml to 30 mg/ml, 11 mg/ml to 30 mg/ml, 12 mg/ml to 30 mg/ml, 13 mg/ml to 30 mg/ml, 14 mg/ml to 30 mg/ml, 15 mg/ml to 30 mg/ml, 16 mg/ml to 30 mg/ml, 17 mg/ml to 30 mg/ml, 18 mg/ml to 30 mg/ml, 19 mg/ml to 30 mg/ml, 20 mg/ml to 30 mg/ml, 21 mg/ml to 30 mg/ml, 22 mg/ml to 30 mg/ml, 23 mg/ml to 30 mg/ml, 24 mg/ml to 30 mg/ml, 25 mg/ml to 30 mg/ml, 26 mg/ml to 30 mg/ml, 27 mg/ml to 30 mg/ml, 28 mg/ml to 30 mg/ml, 29 mg/ml to 30 mg/ml, 10 mg/ml to 29 mg/ml, 11 mg/ml to 29 mg/ml, 12 mg/ml to 29 mg/ml, 13 mg/ml to 29 mg/ml, 14 mg/ml to 29 mg/ml, 15 mg/ml to 29 mg/ml, 16 mg/ml to 29 mg/ml, 17 mg/ml to 29 mg/ml, 18 mg/ml to 29 mg/ml, 19 mg/ml to 29 mg/ml, 20 mg/ml to 29 mg/ml, 21 mg/ml to 29 mg/ml, 22 mg/ml to 29 mg/ml, 23 mg/ml to 29 mg/ml, 24 mg/ml to 29 mg/ml, 25 mg/ml to 29 mg/ml, 26 mg/ml to 29 mg/ml, 27 mg/ml to 29 mg/ml, 28 mg/ml to 29 mg/ml, 10 mg/ml to 28 mg/ml, 11 mg/ml to 28 mg/ml, 12 mg/ml to 28 mg/ml, 13 mg/ml to 28 mg/ml, 14 mg/ml to 28 mg/ml, 15 mg/ml to 28 mg/ml, 16 mg/ml to 28 mg/ml, 17 mg/ml to 28 mg/ml, 18 mg/ml to 28 mg/ml, 19 mg/ml to 28 mg/ml, 20 mg/ml to 28 mg/ml, 21 mg/ml to 28 mg/ml, 22 mg/ml to 28 mg/ml, 23 mg/ml to 28 mg/ml, 24 mg/ml to 28 mg/ml, 25 mg/ml to 28 mg/ml, 26 mg/ml to 28 mg/ml, 27 mg/ml to 28 mg/ml, 10 mg/ml to 27 mg/ml, 11 mg/ml to 27 mg/ml, 12 mg/ml to 27 mg/ml, 13 mg/ml to 27 mg/ml, 14 mg/ml to 27 mg/ml, 15 mg/ml to 27 mg/ml, 16 mg/ml to 27 mg/ml, 17 mg/ml to 27 mg/ml, 18 mg/ml to 27 mg/ml, 19 mg/ml to 27 mg/ml, 20 mg/ml to 27 mg/ml, 21 mg/ml to 27 mg/ml, 22 mg/ml to 27 mg/ml, 23 mg/ml to 27 mg/ml, 24 mg/ml to 27 mg/ml, 25 mg/ml to 27 mg/ml, 26 mg/ml to 27 mg/ml, 10 mg/ml to 26 mg/ml, 11 mg/ml to 26 mg/ml, 12 mg/ml to 26 mg/ml, 13 mg/ml to 26 mg/ml, 14 mg/ml to 26 mg/ml, 15 mg/ml to 26 mg/ml, 16 mg/ml to 26 mg/ml, 17 mg/ml to 26 mg/ml, 18 mg/ml to 26 mg/ml, 19 mg/ml to 26 mg/ml, 20 mg/ml to 26 mg/ml, 21 mg/ml to 26 mg/ml, 22 mg/ml to 26 mg/ml, 23 mg/ml to 26 mg/ml, 24 mg/ml to 26 mg/ml, 25 mg/ml to 26 mg/ml, 10 mg/ml to 25 mg/ml, 11 mg/ml to 25 mg/ml, 12 mg/ml to 25 mg/ml, 13 mg/ml to 25 mg/ml, 14 mg/ml to 25 mg/ml, 15 mg/ml to 25 mg/ml, 16 mg/ml to 25 mg/ml, 17 mg/ml to 25 mg/ml, 18 mg/ml to 25 mg/ml, 19 mg/ml to 25 mg/ml, 20 mg/ml to 25 mg/ml, 21 mg/ml to 25 mg/ml, 22 mg/ml to 25 mg/ml, 23 mg/ml to 25 mg/ml, 24 mg/ml to 25 mg/ml, 10 mg/ml to 24 mg/ml, 11 mg/ml to 24 mg/ml, 12 mg/ml to 24 mg/ml, 13 mg/ml to 24 mg/ml, 14 mg/ml to 24 mg/ml, 15 mg/ml to 24 mg/ml, 16 mg/ml to 24 mg/ml, 17 mg/ml to 24 mg/ml, 18 mg/ml to 24 mg/ml, 19 mg/ml to 24 mg/ml, 20 mg/ml to 24 mg/ml, 21 mg/ml to 24 mg/ml, 22 mg/ml to 24 mg/ml, 23 mg/ml to 24 mg/ml, 10 mg/ml to 23 mg/ml, 11 mg/ml to 23 mg/ml, 12 mg/ml to 23 mg/ml, 13 mg/ml to 23 mg/ml, 14 mg/ml to 23 mg/ml, 15 mg/ml to 23 mg/ml, 16 mg/ml to 23 mg/ml, 17 mg/ml to 23 mg/ml, 18 mg/ml to 23 mg/ml, 19 mg/ml to 23 mg/ml, 20 mg/ml to 23 mg/ml, 21 mg/ml to 23 mg/ml, 22 mg/ml to 23 mg/ml, 10 mg/ml to 22 mg/ml, 11 mg/ml to 22 mg/ml, 12 mg/ml to 22 mg/ml, 13 mg/ml to 22 mg/ml, 14 mg/ml to 22 mg/ml, 15 mg/ml to 22 mg/ml, 16 mg/ml to 22 mg/ml, 17 mg/ml to 22 mg/ml, 18 mg/ml to 22 mg/ml, 19 mg/ml to 22 mg/ml, 20 mg/ml to 22 mg/ml, 21 mg/ml to 22 mg/ml, 10 mg/ml to 21 mg/ml, 11 mg/ml to 21 mg/ml, 12 mg/ml to 21 mg/ml, 13 mg/ml to 21 mg/ml, 14 mg/ml to 21 mg/ml, 15 mg/ml to 21 mg/ml, 16 mg/ml to 21 mg/ml, 17 mg/ml to 21 mg/ml, 18 mg/ml to 21 mg/ml, 19 mg/ml to 21 mg/ml, 20 mg/ml to 21 mg/ml, 10 mg/ml to 20 mg/ml, 11 mg/ml to 20 mg/ml, 12 mg/ml to 20 mg/ml, 13 mg/ml to 20 mg/ml, 14 mg/ml to 20 mg/ml, 15 mg/ml to 20 mg/ml, 16 mg/ml to 20 mg/ml, 17 mg/ml to 20 mg/ml, 18 mg/ml to 20 mg/ml, 19 mg/ml to 20 mg/ml, 10 mg/ml to 19 mg/ml, 11 mg/ml to 19 mg/ml, 12 mg/ml to 19 mg/ml, 13 mg/ml to 19 mg/ml, 14 mg/ml to 19 mg/ml, 15 mg/ml to 19 mg/ml, 16 mg/ml to 19 mg/ml, 17 mg/ml to 19 mg/ml, 18 mg/ml to 19 mg/ml, 10 mg/ml to 18 mg/ml, 11 mg/ml to 18 mg/ml, 12 mg/ml to 18 mg/ml, 13 mg/ml to 18 mg/ml, 14 mg/ml to 18 mg/ml, 15 mg/ml to 18 mg/ml, 16 mg/ml to 18 mg/ml, 17 mg/ml to 18 mg/ml, 10 mg/ml to 17 mg/ml, 11 mg/ml to 17 mg/ml, 12 mg/ml to 17 mg/ml, 13 mg/ml to 17 mg/ml, 14 mg/ml to 17 mg/ml, 15 mg/ml to 17 mg/ml, 16 mg/ml to 17 mg/ml, 10 mg/ml to 16 mg/ml, 11 mg/ml to 16 mg/ml, 12 mg/ml to 16 mg/ml, 13 mg/ml to 16 mg/ml, 14 mg/ml to 16 mg/ml, 15 mg/ml to 16 mg/ml, 10 mg/ml to 15 mg/ml, 11 mg/ml to 15 mg/ml, 12 mg/ml to 15 mg/ml, 13 mg/ml to 15 mg/ml, 14 mg/ml to 15 mg/ml, 10 mg/ml to 14 mg/ml, 11 mg/ml to 14 mg/ml, 12 mg/ml to 14 mg/ml, 13 mg/ml to 14 mg/ml, 10 mg/ml to 13 mg/ml, 11 mg/ml to 13 mg/ml, 12 mg/ml to 13 mg/ml, 10 mg/ml to 12 mg/ml, 11 mg/ml to 12 mg/ml, or about 10 mg/ml to 11 mg/ml. In certain embodiments, the concentration of polyethylene glycol is about 15 mg/ml to about 30 mg/ml. The polyethylene glycol ranges disclosed in this paragraph are hereby disclosed in combination with the medroxyprogesterone and/or docusate sodium ranges disclosed herein. Thus the polyethylene glycol ranges disclosed in this paragraph are hereby disclosed in combination with a medroxyprogesterone concentration of about 260 mg/ml to 440 mg/ml, 260 mg/ml to 340 mg/ml, 270 mg/ml to 330 mg/ml, 280 mg/ml to 320 mg/ml, 290 mg/ml to 310 mg/ml, 295 mg/ml to 305 mg/ml, 370 mg/ml to 430 mg/ml, 380 mg/ml to 420 mg/ml, 390 mg/ml to 410 mg/ml, 395 mg/ml to 405 mg/ml, and a docusate sodium concentration of about 0.5 mg/ml to about 3 mg/ml, about 0.5 mg/ml to about 1.0 mg/ml or about 0.5 mg/ml to about 0.7 mg/ml. For the sake of brevity, all of the combinations are not being parsed out.

For example, the concentrations of polyethylene glycol (mg/ml) in the compositions of the disclosure preferably may be about 15, 16, 17, 18, 19, 20, 21, 22, 23, 24, 25, 26, 27, 28, 29, or about 30 mg/ml. The polyethylene glycol ranges disclosed in this paragraph are hereby disclosed in combination with the medroxyprogesterone and/or docusate sodium ranges disclosed herein. Thus the polyethylene glycol ranges disclosed in this paragraph are hereby disclosed in combination with a medroxyprogesterone concentration of about 260 mg/ml to 340 mg/ml, 270 mg/ml to 330 mg/ml, 280 mg/ml to 320 mg/ml, 290 mg/ml to 310 mg/ml, 295 mg/ml to 305 mg/ml, 360 mg/ml to 440 mg/ml, 370 mg/ml to 430 mg/ml, 380 mg/ml to 420 mg/ml, 390 mg/ml to 410 mg/ml, 395 mg/ml to 405 mg/ml, and a docusate sodium concentration of about 0.5 mg/ml to 1.5 mg/ml. For the sake of brevity, all of the combinations are not being parsed out.

In preferred aspects, the compositions described herein comprise medroxyprogesterone acetate at a concentration of about 260 mg/ml to about 340 mg/ml, docusate sodium at a concentration of about 0.5 mg/ml to about 3.0 mg/ml, and polyethylene glycol at a concentration of about 10 mg/ml to about 40 mg/ml. In further preferred aspects, the compositions described herein comprise medroxyprogesterone acetate at a concentration of about 260 mg/ml to about 340 mg/ml, docusate sodium at a concentration of about 0.5 mg/ml to about 1.0 mg/ml, and polyethylene glycol at a concentration of about 15 mg/ml to about 25 mg/ml. In still further preferred aspects, the compositions described herein comprise medroxyprogesterone acetate at a concentration of about 260 mg/ml to about 340 mg/ml, docusate sodium at a concentration of about 0.5 mg/ml to about 0.7 mg/ml, and polyethylene glycol at a concentration of about 15 mg/ml to about 25 mg/ml.

In other preferred aspects, the compositions described herein comprise medroxyprogesterone acetate at a concentration of about 270 mg/ml to about 330 mg/ml, docusate sodium at a concentration of about 0.5 mg/ml to about 3.0 mg/ml, and polyethylene glycol at a concentration of about 10 mg/ml to about 40 mg/ml. In further preferred aspects, the compositions described herein comprise medroxyprogesterone acetate at a concentration of about 270 mg/ml to about 330 mg/ml, docusate sodium at a concentration of about 0.5 mg/ml to about 1.0 mg/ml, and polyethylene glycol at a concentration of about 15 mg/ml to about 25 mg/ml. In still further preferred aspects, the compositions described herein comprise medroxyprogesterone acetate at a concentration of about 270 mg/ml to about 330 mg/ml, docusate sodium at a concentration of about 0.5 mg/ml to about 0.7 mg/ml, and polyethylene glycol at a concentration of about 15 mg/ml to about 25 mg/ml.

In still other preferred aspects, the compositions described herein comprise medroxyprogesterone acetate at a concentration of about 280 mg/ml to about 320 mg/ml, docusate sodium at a concentration of about 0.5 mg/ml to about 1.0 mg/ml, and polyethylene glycol at a concentration of about 10 mg/ml to about 40 mg/ml. In further preferred aspects, the compositions described herein comprise medroxyprogesterone acetate at a concentration of about 280 mg/ml to about 340 mg/ml, docusate sodium at a concentration of about 0.5 mg/ml to about 1.0 mg/ml, and polyethylene glycol at a concentration of about 15 mg/ml to about 25 mg/ml. In still further preferred aspects, the compositions described herein comprise medroxyprogesterone acetate at a concentration of about 280 mg/ml to about 340 mg/ml, docusate sodium at a concentration of about 0.5 mg/ml to about 0.7 mg/ml, and polyethylene glycol at a concentration of about 15 mg/ml to about 25 mg/ml.

In additional preferred aspects, the compositions described herein comprise medroxyprogesterone acetate at a concentration of about 290 mg/ml to about 310 mg/ml, docusate sodium at a concentration of about 0.5 mg/ml to about 3.0 mg/ml, and polyethylene glycol at a concentration of about 10 mg/ml to about 40 mg/ml. In further preferred aspects, the compositions described herein comprise medroxyprogesterone acetate at a concentration of about 290 mg/ml to about 310 mg/ml, docusate sodium at a concentration of about 0.5 mg/ml to about 3.0 mg/ml, and polyethylene glycol at a concentration of about 15 mg/ml to about 25 mg/ml. In still further preferred aspects, the compositions described herein comprise medroxyprogesterone acetate at a concentration of about 290 mg/ml to about 310 mg/ml, docusate sodium at a concentration of about 0.5 mg/ml to about 0.7 mg/ml, and polyethylene glycol at a concentration of about 15 mg/ml to about 25 mg/ml.

In still additional preferred aspects, the compositions described herein comprise medroxyprogesterone acetate at a concentration of about 295 mg/ml to about 305 mg/ml, docusate sodium at a concentration of about 0.5 mg/ml to about 3.0 mg/ml, and polyethylene glycol at a concentration of about 10 mg/ml to about 40 mg/ml. In further preferred aspects, the compositions described herein comprise medroxyprogesterone acetate at a concentration of about 295 mg/ml to about 305 mg/ml, docusate sodium at a concentration of about 0.5 mg/ml to about 1.0 mg/ml, and polyethylene glycol at a concentration of about 15 mg/ml to about 25 mg/ml. In still further preferred aspects, the compositions described herein comprise medroxyprogesterone acetate at a concentration of about 295 mg/ml to about 305 mg/ml, docusate sodium at a concentration of about 0.5 mg/ml to about 0.7 mg/ml, and polyethylene glycol at a concentration of about 15 mg/ml to about 25 mg/ml.

In preferred aspects, the compositions described herein comprise medroxyprogesterone acetate at a concentration of about 360 mg/ml to about 440 mg/ml, docusate sodium at a concentration of about 0.5 mg/ml to about 3.0 mg/ml, and polyethylene glycol at a concentration of about 10 mg/ml to about 40 mg/ml. In further preferred aspects, the compositions described herein comprise medroxyprogesterone acetate at a concentration of about 360 mg/ml to about 440 mg/ml, docusate sodium at a concentration of about 0.5 mg/ml to about 1.5 mg/ml, and polyethylene glycol at a concentration of about 15 mg/ml to about 25 mg/ml. In still further preferred aspects, the compositions described herein comprise medroxyprogesterone acetate at a concentration of about 360 mg/ml to about 440 mg/ml, docusate sodium at a concentration of about 0.5 mg/ml to about 0.7 mg/ml, and polyethylene glycol at a concentration of about 15 mg/ml to about 25 mg/ml.

In other preferred aspects, the compositions described herein comprise medroxyprogesterone acetate at a concentration of about 370 mg/ml to about 430 mg/ml, docusate sodium at a concentration of about 0.5 mg/ml to about 3.0 mg/ml, and polyethylene glycol at a concentration of about 10 mg/ml to about 40 mg/ml. In further preferred aspects, the compositions described herein comprise medroxyprogesterone acetate at a concentration of about v, docusate sodium at a concentration of about 0.5 mg/ml to about 1.5 mg/ml, and polyethylene glycol at a concentration of about 15 mg/ml to about 25 mg/ml. In still further preferred aspects, the compositions described herein comprise medroxyprogesterone acetate at a concentration of about 370 mg/ml to about 430 mg/ml, docusate sodium at a concentration of about 0.5 mg/ml to about 0.7 mg/ml, and polyethylene glycol at a concentration of about 15 mg/ml to about 25 mg/ml.

In still other preferred aspects, the compositions described herein comprise medroxyprogesterone acetate at a concentration of about 380 mg/ml to about 420 mg/ml, docusate sodium at a concentration of about 0.5 mg/ml to about 1.0 mg/ml, and polyethylene glycol at a concentration of about 10 mg/ml to about 40 mg/ml. In further preferred aspects, the compositions described herein comprise medroxyprogesterone acetate at a concentration of about 380 mg/ml to about 420 mg/ml, docusate sodium at a concentration of about 0.5 mg/ml to about 1.5 mg/ml, and polyethylene glycol at a concentration of about 15 mg/ml to about 25 mg/ml. In still further preferred aspects, the compositions described herein comprise medroxyprogesterone acetate at a concentration of about 380 mg/ml to about 420 mg/ml, docusate sodium at a concentration of about 0.5 mg/ml to about 0.7 mg/ml, and polyethylene glycol at a concentration of about 15 mg/ml to about 25 mg/ml.

In additional preferred aspects, the compositions described herein comprise medroxyprogesterone acetate at a concentration of about 390 mg/ml to about 410 mg/ml, docusate sodium at a concentration of about 0.5 mg/ml to about 3.0 mg/ml, and polyethylene glycol at a concentration of about 10 mg/ml to about 40 mg/ml. In further preferred aspects, the compositions described herein comprise medroxyprogesterone acetate at a concentration of about 390 mg/ml to about 410 mg/ml, docusate sodium at a concentration of about 0.5 mg/ml to about 1.5 mg/ml, and polyethylene glycol at a concentration of about 15 mg/ml to about 25 mg/ml. In still further preferred aspects, the compositions described herein comprise medroxyprogesterone acetate at a concentration of about 390 mg/ml to about 410 mg/ml, docusate sodium at a concentration of about 0.5 mg/ml to about 0.7 mg/ml, and polyethylene glycol at a concentration of about 15 mg/ml to about 25 mg/ml.

In still additional preferred aspects, the compositions described herein comprise medroxyprogesterone acetate at a concentration of about 395 mg/ml to about 405 mg/ml, docusate sodium at a concentration of about 0.5 mg/ml to about 3.0 mg/ml, and polyethylene glycol at a concentration of about 10 mg/ml to about 40 mg/ml. In further preferred aspects, the compositions described herein comprise medroxyprogesterone acetate at a concentration of about 395 mg/ml to about 405 mg/ml, docusate sodium at a concentration of about 0.5 mg/ml to about 1.5 mg/ml, and polyethylene glycol at a concentration of about 15 mg/ml to about 25 mg/ml. In still further preferred aspects, the compositions described herein comprise medroxyprogesterone acetate at a concentration of about 395 mg/ml to about 405 mg/ml, docusate sodium at a concentration of about 0.5 mg/ml to about 0.7 mg/ml, and polyethylene glycol at a concentration of about 15 mg/ml to about 25 mg/ml. By way of further example, the compositions described herein comprise medroxyprogesterone acetate at a concentration of about 400 mg/ml, docusate sodium at a concentration of about 0.6 mg/ml and polyethylene glycol at a concentration of about 20 mg/ml. As a further example, the compositions described herein comprise medroxyprogesterone acetate at a concentration of about 400 mg/ml, docusate sodium at a concentration of about 1.3 mg/ml and polyethylene glycol at a concentration of about 28 mg/ml. As a further example, the compositions described herein comprise medroxyprogesterone acetate at a concentration of about 400 mg/ml, docusate sodium at a concentration of about 1.3 mg/ml and polyethylene glycol at a concentration of about 20 mg/ml. By way of further example, the compositions described herein comprise medroxyprogesterone acetate at a concentration of about 400 mg/ml, docusate sodium at a concentration of about 1.0 mg/ml and polyethylene glycol at a concentration of about 20 mg/ml. As a further example, the compositions described herein comprise medroxyprogesterone acetate at a concentration of about 300 mg/ml, docusate sodium at a concentration of about 0.6 mg/ml and polyethylene glycol at a concentration of about 20 mg/ml. By way of further example, the compositions described herein comprise medroxyprogesterone acetate at a concentration of about 300 mg/ml, docusate sodium at a concentration of about 1.0 mg/ml and polyethylene glycol at a concentration of about 20 mg/ml.

By way of further example, the compositions described herein comprise medroxyprogesterone acetate at a concentration of about 400 mg/ml and docusate sodium at a concentration of about 0.6 mg/ml. As a further example, the compositions described herein comprise medroxyprogesterone acetate at a concentration of about 400 mg/ml and docusate sodium at a concentration of about 1.3 mg/ml. As a further example, the compositions described herein comprise medroxyprogesterone acetate at a concentration of about 400 mg/ml and docusate sodium at a concentration of about 1.0 mg/ml.

By way of further example, compositions described herein comprise medroxyprogesterone acetate at a concentration of about 400 mg/ml and docusate sodium at a concentration of about 0.6 mg/ml and polyethylene glycol at a concentration of about 15 mg/ml to about 30 mg/ml. As a further example, compositions described herein comprise medroxyprogesterone acetate at a concentration of about 400 mg/ml and docusate sodium at a concentration of about 0.6 mg/ml and polyethylene glycol at a concentration of about 20 mg/ml. As a further example, compositions described herein comprise medroxyprogesterone acetate at a concentration of about 400 mg/ml and docusate sodium at a concentration of about 0.6 mg/ml and polyethylene glycol at a concentration of about 28 mg/ml.

By way of further example, compositions described herein comprise medroxyprogesterone acetate at a concentration of about 400 mg/ml and docusate sodium at a concentration of about 1.3 mg/ml and polyethylene glycol at a concentration of about 15 mg/ml to about 30 mg/ml. As a further example, compositions described herein comprise medroxyprogesterone acetate at a concentration of about 400 mg/ml and docusate sodium at a concentration of about 1.3 mg/ml and polyethylene glycol at a concentration of about 20 mg/ml. As a further example, compositions described herein comprise medroxyprogesterone acetate at a concentration of about 400 mg/ml and docusate sodium at a concentration of about 1.3 mg/ml and polyethylene glycol at a concentration of about 28 mg/ml.

By way of further example, compositions described herein comprise medroxyprogesterone acetate at a concentration of about 400 mg/ml and docusate sodium at a concentration of about 1.0 mg/ml and polyethylene glycol at a concentration of about 15 mg/ml to about 30 mg/ml. As a further example, compositions described herein comprise medroxyprogesterone acetate at a concentration of about 400 mg/ml and docusate sodium at a concentration of about 1.0 mg/ml and polyethylene glycol at a concentration of about 20 mg/ml. As a further example, compositions described herein comprise medroxyprogesterone acetate at a concentration of about 400 mg/ml and docusate sodium at a concentration of about 1.0 mg/ml and polyethylene glycol at a concentration of about 28 mg/ml.

By way of further example, the compositions described herein comprise medroxyprogesterone acetate at a concentration of about 300 mg/ml and docusate sodium at a concentration of about 0.6 mg/ml. As a further example, the compositions described herein comprise medroxyprogesterone acetate at a concentration of about 300 mg/ml and docusate sodium at a concentration of about 1.3 mg/ml. As a further example, the compositions described herein comprise medroxyprogesterone acetate at a concentration of about 300 mg/ml and docusate sodium at a concentration of about 1.0 mg/ml.

By way of further example, compositions described herein comprise medroxyprogesterone acetate at a concentration of about 300 mg/ml and docusate sodium at a concentration of about 0.6 mg/ml and polyethylene glycol at a concentration of about 15 mg/ml to about 30 mg/ml. As a further example, compositions described herein comprise medroxyprogesterone acetate at a concentration of about 300 mg/ml and docusate sodium at a concentration of about 0.6 mg/ml and polyethylene glycol at a concentration of about 20 mg/ml. As a further example, compositions described herein comprise medroxyprogesterone acetate at a concentration of about 300 mg/ml and docusate sodium at a concentration of about 0.6 mg/ml and polyethylene glycol at a concentration of about 28 mg/ml.

By way of further example, compositions described herein comprise medroxyprogesterone acetate at a concentration of about 300 mg/ml and docusate sodium at a concentration of about 1.3 mg/ml and polyethylene glycol at a concentration of about 15 mg/ml to about 30 mg/ml. As a further example, compositions described herein comprise medroxyprogesterone acetate at a concentration of about 300 mg/ml and docusate sodium at a concentration of about 1.3 mg/ml and polyethylene glycol at a concentration of about 20 mg/ml. As a further example, compositions described herein comprise medroxyprogesterone acetate at a concentration of about 300 mg/ml and docusate sodium at a concentration of about 1.3 mg/ml and polyethylene glycol at a concentration of about 28 mg/ml.

By way of further example, compositions described herein comprise medroxyprogesterone acetate at a concentration of about 300 mg/ml and docusate sodium at a concentration of about 1.0 mg/ml and polyethylene glycol at a concentration of about 15 mg/ml to about 30 mg/ml. As a further example, compositions described herein comprise medroxyprogesterone acetate at a concentration of about 300 mg/ml and docusate sodium at a concentration of about 1.0 mg/ml and polyethylene glycol at a concentration of about 20 mg/ml. As a further example, compositions described herein comprise medroxyprogesterone acetate at a concentration of about 300 mg/ml and docusate sodium at a concentration of about 1.0 mg/ml and polyethylene glycol at a concentration of about 28 mg/ml.

In some embodiments of the disclosure, the medroxyprogesterone acetate is annealed. As used herein, "annealed" signifies the process of simultaneous dissolution and recrystallization of particles in solvent that alters surface area of particles.

Preferably, the compositions of the disclosure will provide a minimum, maximum and mean plasma concentration of MPA in a human, preferably a female, more preferably a female who has experienced at least one menses, over a particular time period post administration, e.g. subcutaneous injection. The minimum, maximum and mean MPA level will be sufficient to suppress ovulation in the human female for the duration of the time period. In preferred embodiments, the time period is about 182 days, for example, about 6 months.

Methods of measuring human MPA levels are known in the art. In certain embodiments, the mean MPA plasma concentration in a human, preferably a female, more preferably a female who has experienced at least one menses, is about 0.40 ng/mL at 28 days post administration, e.g. subcutaneous injection. In certain embodiments, the composition provides MPA plasma concentration in a human, preferably a female, more preferably a female who has experienced at least one menses, of about 0.03 ng/mL to 0.50 ng/ml at 28 days post administration, e.g. subcutaneous injection. In certain embodiments, the composition provides a mean MPA plasma concentration in a human, preferably a female, more preferably a female who has experienced at least one menses, of about 0.40 ng/mL, at 91 days post administration, e.g. subcutaneous injection. In certain embodiments, the composition exhibits a MPA plasma concentration in a human, preferably a female, more preferably a female who has experienced at least one menses, of about 0.25 ng/mL to about 0.65 ng/ml at 91 days post administration, e.g. subcutaneous injection. In certain embodiments, the composition exhibits a mean MPA plasma concentration in a human, preferably a female, more preferably a female who has experienced at least one menses, of about 0.20 ng/ml at 182 days post administration, e.g. subcutaneous injection. In certain embodiments, the composition exhibits MPA plasma concentration in a human, preferably a female, more preferably a female who has experienced at least one menses, of about 0.15 ng/mL to about 0.35 ng/ml at 182 days post administration, e.g. subcutaneous injection.

In other preferred embodiments, the compositions of the disclosure will exhibit a minimum, maximum and mean area under the plasma concentration time curve (AUC) of MPA in a human, preferably a female, more preferably a female who has experienced at least one menses, over a particular time period post administration, e.g. subcutaneous injection. The minimum, maximum and mean AUC of MPA will be sufficient to suppress ovulation in the human female for the duration of the time period. In preferred embodiments, the time period is about 182 days, e.g., about 6 months.

In certain embodiments, the composition provides a mean AUC of MPA in a human, preferably a female, more preferably a female who has experienced at least one menses, of about 10.00 ng/mL over a time period of 28 days or a time period of about 28 days post administration, e.g. subcutaneous injection. In certain embodiments, the composition provides an AUC of MPA in a human, preferably a female, more preferably a female who has experienced at least one menses, of about 7.80 ng/mL to about 14.50 ng/ml over a time period of 28 days or a time period of about 28 days post administration, e.g. subcutaneous injection. In certain embodiments, the composition provides a mean AUC of MPA in a human, preferably a female, more preferably a female who has experienced at least one menses, of about 34.50 ng/mL over a time period of 91 days or a time period of about 91 days post administration, e.g. subcutaneous injection. In certain embodiments, the composition exhibits an AUC of MPA in a human, preferably a female, more preferably a female who has experienced at least one menses, of about 23.40 ng/mL to about 44.00 ng/ml over a time period of 91 days or a time period of about 91 days post administration, e.g. subcutaneous injection. In certain embodiments, the composition provides a mean AUC of MPA in a human, preferably a female, more preferably a female who has experienced at least one menses, of about 60.20 ng/ml over a time period of 182 days or a time period of about 182 days post administration, e.g. subcutaneous injection. In certain embodiments, the composition provides an AUC of MPA in a human, preferably a female, more preferably a female who has experienced at least one menses, of about 38.60 ng/mL to about 84.90 ng/ml over a time period of 182 days or a time period of about 182 days post administration, e.g. subcutaneous injection.

In certain embodiments, the compositions of the disclosure provide a mean plasma concentration of about 0.40 ng/ml at about 28 days post subcutaneous injection. In certain embodiments, the compositions of the disclosure provide a plasma concentration of about 0.03 ng/ml to about 0.50 ng/ml at about 28 days post subcutaneous injection. In certain embodiments, the compositions of the disclosure provide a mean plasma concentration of about 0.40 ng/ml at about 91 days post subcutaneous injection. In certain embodiments, the compositions of the disclosure provide a plasma concentration of about 0.25 ng/ml to about 0.65 ng/ml at about 91 days post subcutaneous injection. In certain embodiments, the compositions of the disclosure provide a mean plasma concentration of about 0.20 ng/ml at about 182 days post subcutaneous injection. In certain embodiments, the compositions of the disclosure provide a plasma concentration of about 0.15 ng/ml to about 0.35 ng/ml at about 182 days post subcutaneous injection. In certain embodiments, the compositions of the disclosure provide a mean AUC of about 10.00 ng/ml at about 28 days post subcutaneous injection. In certain embodiments, the compositions of the disclosure provide an AUC of about 7.80 ng/ml to about 14.50 ng/ml at about 28 days post subcutaneous injection. In certain embodiments, the compositions of the disclosure provide a mean AUC of about 34.50 ng/ml at about 91 days post subcutaneous injection. In certain embodiments, the compositions of the disclosure provide a AUC of about 23.40 ng/ml to about 44.00 ng/ml at about 91 days post subcutaneous injection. In certain embodiments, the compositions of the disclosure provide a mean AUC of about 60.20 ng/ml at about 182 days post subcutaneous injection. In certain embodiments, the compositions of the disclosure provide a plasma concentration of about 38.60 ng/ml to about 84.90 ng/ml at about 182 days post subcutaneous injection. The compositions of the disclosure also include water. The water used in the compositions is preferably sterile water for injection.

In some embodiments of the disclosure, the compositions may further comprise tonicity adjusters such as sulfate salts or sodium salts. Sulfate salts include, for example, sodium sulfate (e.g., sodium sulfate anhydrous) or magnesium sulfate (e.g., magnesium sulfate heptahydrate), as well as combinations thereof. Sodium salts include, for example, sodium chloride.

In some embodiments of the disclosure, the compositions may further comprise a stabilizer. As used herein, "stabilizer" refers to a stabilizing compound or combination of stabilizing compounds which maintain the pH of the composition. Examples of stabilizers that may be useful in the present compositions include, without limitation, thioglycerol, monothioglycerol, lipoic acid, propyl gallate, cysteine, sodium formaldehyde sulfoxylate, or dihydrolipoic acid, and methionine (e.g., L-methionine), as well as combinations thereof. Preferred stabilizers include, without limitation, monothioglycerol, cysteine, sodium formaldehyde sulfoxylate, or methionine. An exemplary stabilizer is methionine.

In some embodiments of the disclosure, the compositions may further comprise buffering salts. Examples of buffering salts that may be useful in the present compositions include phosphate salts, acetate salts, citrate salts, tartrate salts, lactate salts, succinate salts, maleate salts, and histidine salts, as known in the art. In preferred embodiments, the buffering salt is a phosphate salt including, for example, monobasic sodium phosphate, dibasic sodium phosphate, or a combination thereof.

In preferred aspects of the disclosure, the compositions further comprise sodium sulfate, methionine, monobasic sodium phosphate, and dibasic sodium phosphate. Exemplary compositions of the disclosure comprise medroxyprogesterone acetate, docusate sodium, polyethylene glycol, water, sodium sulfate, methionine, monobasic sodium phosphate, and dibasic sodium phosphate.

In addition to the medroxyprogesterone acetate and foregoing ingredients, the compositions of the disclosure may comprise one or more additional pharmaceutically acceptable excipients. "Excipient" means the substances used to formulate active pharmaceutical ingredients (API) into pharmaceutical formulations or compositions; in a preferred embodiment, an excipient does not lower or interfere with the primary therapeutic effect of the API. Preferably, an excipient is therapeutically inert. The term "excipient" encompasses carriers, diluents, vehicles, solubilizers, stabilizers, bulking agents, and binders. Excipients can also be those substances present in a pharmaceutical formulation as an indirect or unintended result of the manufacturing process. Preferably, excipients are approved for or considered to be safe for human and animal administration, i.e., GRAS substances (generally regarded as safe). GRAS substances are listed by the Food and Drug administration in the Code of Federal Regulations (CFR) at 21 CFR § 182 and 21 CFR § 184, incorporated herein by reference.

The excipients can be included in the compositions described herein and in the final dosage forms described herein. One would be able to select one or more suitable excipients using skill in the art and the teachings herein. In some embodiments, the excipients may be selected from those described in Handbook of Pharmaceutical Excipients, 5th ed. (2006). In preferred embodiments, the excipient includes, without limitation, one or more of a suspending agent, surfactant, tonicity adjuster, stabilizer, buffer, vehicle, or a combination thereof.

In some aspects of the disclosure, the pH of the composition is about 4.0 to about 7.0. In some embodiments of the disclosure, the pH of the composition is about 6.0 to about 7.0. For example, the pH of the composition is about 4.0, 4.5, 5.0, 5.5, 6.0, 6.5, or about 7.0. In preferred embodiments, the pH of the composition is about 6.6 to about 6.7. It is advantageous for the pH of the composition to not decrease during storage so that the composition may be safely administered to patients without generating significant pain.

B. Dosage Forms

Suitable dosage forms include, but are not limited to oral, rectal, sub-lingual, mucosal, nasal, ophthalmic, subcutaneous, intramuscular, intravenous, transdermal, spinal, intrathecal, intraarticular, intra-arterial, sub-arachnoid, bronchial, lymphatic, and intra-uterine administration, and other dosage forms for systemic delivery of active ingredients. In a preferred embodiment, the dosage form is suitable for subcutaneous injection. The compositions may be administered with a syringe-needle suitable for subcutaneous use. As used herein, the term "subcutaneous" means under the skin, and is understood by those of skill in the art to be interchangeable with the term subdermal.

Compositions of the disclosure can be provided a single unit dosage forms. A "single unit dose" as used herein means the pharmaceutical compositions disclosed herein being in a container and in an amount suitable for reconstitution and/or administration of a single dose, wherein the amount suitable for reconstitution and administration of a single dose is a therapeutically effective amount. The single unit dose, although typically in the form of a vial, may be any suitable container, such as ampoules, syringes (e.g., pre-filled syringes), co-vials, cartridges, which are capable of maintaining a sterile environment. Such containers can be glass or plastic, provided that the material does not act with the medroxyprogesterone acetate compositions. The closure is typically a stopper, most typically a sterile rubber stopper, which affords a hermetic seal. In some embodiments, the composition is supplied as a white suspension packed in a 3 mL United States Pharmacopeia (USP) Type 1 clear glass borosilicate vial closed with a 13 mm chlorobutyl siliconized rubber stopper and aluminum cap, fitted with an orange color flip-off disk. In some embodiments, the vial is filled with about 1.183 mL to about 1.345 mL of the compositions. For example, the volume of compositions can comprise about 1.18, 1.19, 1.20, 1.21, 1.22, 1.23, 1.24, 1.25, 1.26, 1.27, 1.28, 1.29, 1.30, 1.31, 1.32, 1.33 or 1.34 mL. Preferably, the volume of the composition is about 1.26 mL. In all cases, the ultimate dosage form should be sterile, fluid and stable under the conditions of manufacture and storage. In some embodiments, the composition is supplied as a white suspension packed in a BD Uniject™ (PATH Org.) single dose, disposable, auto-disable (non-syringe) pre-fillable injection system for intramuscular (IM) or subcutaneous (SC) injections. In an embodiment, the pre-filled Uniject™ may be packed in an aluminum foil pouch. In some embodiments, the Uniject™ is filled with about 0.1 ml to about 2.0 ml of a composition, about 0.5 ml to about 1.5 ml or about 1 ml, disclosed herein.

As used herein, the term "vial" refers to any walled container, whether rigid or flexible.

"Therapeutically effective amount" refers to an amount of an active pharmaceutical agent described herein which is sufficient to inhibit, halt, or cause an improvement in a disorder or condition being treated in a particular subject or subject population. In certain embodiments, in a human or other mammal, a therapeutically effective amount can be determined experimentally in a laboratory or clinical setting or may be the amount required by government guidelines for the particular disease and subject being treated. It should be appreciated that determination of proper dosage forms, dosage amounts, and routes of administration is within the level of ordinary skill in the pharmaceutical and medical arts.

C. Treatment Methods

The compositions described herein may be employed in methods for preventing pregnancy. The compositions described herein can also be used for treating endometriosis-associated pain. In other aspects, the compositions can be used to treat renal carcinoma. In still other aspects, the compositions can be used to treat endometrial carcinoma. As used herein, "patient" and "subject" are used interchangeably and are intended to mean a mammal. Thus, the compositions described herein are applicable to human and nonhuman subjects. In certain embodiments, the compositions described herein are applicable to humans. In some embodiments, the patient is a female.

"Treatment" refers to the acute or prophylactic diminishment or alleviation of at least one symptom or characteristic associated or caused by a disorder being treated. In certain embodiments, treatment can include diminishment of several symptoms of a disorder or complete eradication of a disorder.

As used herein, "preventing pregnancy" refers to the suppression of ovulation in women of childbearing potential, where ovulation is defined as a single elevated serum progesterone level. In preferred embodiments, an increase in progesterone of 3 to 5 ng/mL sustained over at least 5 days indicates ovulation.

"Endometriosis-associated pain" as used herein refers to the pain caused when the tissue lining the inside of the uterus (the endometrium) grows outside of the uterus.

"Renal carcinoma" refers to a cancer that originates in the kidney, commonly originating in the lining of the renal tubules. "Endometrial carcinoma" refers to a cancer that originates in the uterus, specifically originating in the endometrial cells forming the lining of the uterus.

Accordingly, the methods of using the compositions described herein have a wide-sweeping use in the treatment of a variety of indications. The use of the compositions does not depend on the method of use. In some embodiments, the disorder or condition being treated is acute, chronic, or a combination thereof.

The methods include administering to the patient the compositions described herein. The methods may also include identifying a patient in need of treatment with medroxyprogesterone acetate. Determination of the proper dosage of the active pharmaceutical agent discussed herein for a particular situation is within the skill of the practitioner.

In some aspects, provided is a method for preventing pregnancy or for treating endometriosis-associated pain, or endometrial carcinoma in a female subject, or for treating renal carcinoma in a subject, the method including the step of subcutaneously administering a composition comprising medroxyprogesterone acetate at a concentration of about 360 mg/ml to about 440 mg/ml and docusate sodium at a concentration of about 0.5 mg/ml to about 3.0 mg/ml and further comprising PEG at a concentration of about 10 to about 30 mg/ml. In some embodiments, MPA is present in the composition at a concentration of 370 mg/ml to about 430 mg/ml, about 380 mg/ml to about 420 mg/ml, about 390 mg/ml to about 410 mg/ml, about 395 mg/ml to about 405 mg/ml, or about 400 mg/ml. In some embodiments, docusate sodium is present at a concentration of about 0.5 mg/ml to about 1.3 mg/ml.

In some aspects, provided is a method for preventing pregnancy or for treating endometriosis-associated pain, or endometrial carcinoma in a female subject, or for treating renal carcinoma in a subject, the method including the step of subcutaneously administering a composition comprising medroxyprogesterone acetate at a concentration of about 260 mg/ml to about 340 mg/ml and docusate sodium at a concentration of about 0.5 mg/ml to about 3.0 mg/ml and further comprising PEG at a concentration of about 10 to about 30 mg/ml. In some embodiments, MPA is present in the composition at a concentration of 270 mg/ml to about 330 mg/ml, about 280 mg/ml to about 320 mg/ml, about 290 mg/ml to about 310 mg/ml, about 295 mg/ml to about 305 mg/ml, or about 300 mg/ml. In some embodiments, docusate sodium is present at a concentration of about 0.5 mg/ml to about 1.0 mg/ml. In further embodiments, docusate sodium is present at a concentration of about 0.5 mg/ml to about 0.7 mg/ml.

D. Stability

The invention provides stable, pharmaceutically acceptable compositions comprising medroxyprogesterone acetate. In particular, the disclosure provides compositions which may be administered about once every four months, about once every five months or about once every six months. An aspect of the disclosure is conditions and means for enhancing the stability of the medroxyprogesterone acetate composition upon shelf storage and/or upon reconstitution.

"Stable pharmaceutical composition" refers to any pharmaceutical composition having sufficient stability to have utility as a pharmaceutical product. Preferably, a stable pharmaceutical composition has sufficient stability to allow storage at a convenient temperature, preferably between −20° C. and 40° C., more preferably about 2° C. to about 30° C., for a reasonable period of time, e.g., the shelf-life of the product which can be as short as one month but is typically six months or longer, more preferably one year or longer even more preferably twenty-four months or longer, and even more preferably thirty-six months or longer. The shelf-life or expiration can be that amount of time where the active ingredient degrades to a point below 90% purity. For purposes of the present invention stable pharmaceutical composition includes reference to pharmaceutical compositions with specific ranges of impurities as described herein. Preferably, a stable pharmaceutical composition is one which has minimal degradation of the active ingredient, e.g., it retains at least about 85% of un-degraded active, preferably at least about 90%, and more preferably at least about 95%, after storage at 2-30° C. for a 2-3 year period of time.

The "zeta potential" of the composition refers to the potential difference between the dispersion medium and the layer of medium attached to the MPA drug particle, as measured in millivolts (mV). For example, a composition with a high zeta potential (mV negative or positive) may exhibit less particle aggregation than a composition with a lower zeta potential (mV negative or positive).

"Degraded" as used herein means that the active ingredient has undergone a change in chemical structure.

"Controlling" as used herein means putting process controls in place to facilitate achievement of the thing being controlled. For example, in a given case, "controlling" can mean testing samples of each lot or a number of lots regularly or randomly or selecting process conditions so as to facilitate regulatory approval of a pharmaceutical product by a regulatory agency, such as the U.S. Food and Drug Administration and similar agencies in other countries or regions.

The term "pharmaceutically acceptable" as used herein means that the thing that is pharmaceutically acceptable, e.g., components, including containers, of a pharmaceutical composition, does not cause unacceptable loss of pharmacological activity or unacceptable adverse side effects. Examples of pharmaceutically acceptable components are provided in The United States Pharmacopeia (USP), The National Formulary (NF), adopted at the United States Pharmacopeial Convention, held in Rockville, Md. in 1990 and FDA Inactive Ingredient Guide 1990, 1996 issued by the U.S. Food and Drug Administration (both are hereby incorporated by reference herein, including any drawings). Other grades of solutions or components that meet necessary limits and/or specifications that are outside of the USP/NF may also be used.

As used herein, "storage condition" refers to the number of months the compositions are stored at a given temperature with a given humidity in either an upright (U) or inverted (I) position. In some embodiments of the disclosure, the compositions may be stored from a range of 0 to 6 months. For example, compositions may be stored for about 0, 1, 2, 3, 4, 5, or about 6 months. In some embodiments of the disclosure, the composition may be stored at a range of temperatures from about 25 to about 60° C. For example, the compositions may be stored at about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or about 60° C. In some embodiments, the compositions may be stored at a range of humidity percentages from about 60 to about 75 percent humidity. For example, the compositions may be stored at about 60, 61, 62, 63, 64, 65, 66, 67, 68, 69, 70, 71, 72, 73, 74 or about 75 percent humidity. In some embodiments of the disclosure, the compositions are stable when stored upright or inverted.

As used herein, "PSD" refers to particle-size distribution of particles in a fluid. Dx(N) refers to the mathematical function wherein "x" represents volume distribution while "N" represents percentage of particles with a diameter less than declared value. For example, Dx(10) is the diameter at which 10% of the sample's volume is comprised of particles with a diameter less than this value. Dx(50) is the diameter at which 50% of the sample's volume is comprised of particles with a diameter less than this value. Dx(90) is the diameter at which 90% of the sample's volume is comprised of particles with a diameter less than this value.

As used herein, "impurities" means the impurities in the composition as measured by high performance liquid chromatography (HPLC) as compared to a reference or control. Impurities may include, for example, acetoxyprogesterone, medroxyprogesterone, megestrol acetate, 6β-Methyl-acetoxyprogestrone or acetoxyprogesterone-6-methylene.

As used herein, "resuspendability" means dispersing the composition by shaking and comparing to the description of the product. If the appearance matches the description with no signs of caking or agglomerated particles, it conforms. Compositions of the disclosure are resuspendable within about 10 seconds to about 300 seconds. In some aspects, compositions of the disclosure are resuspendable within about 10 seconds to about 200 seconds. In some aspects, compositions of the disclosure are resuspendable within about 10 seconds to about 50 seconds. In some aspects, the compositions of the disclosure are resuspendable within about 10 seconds to 40 seconds and preferably not more than (NMT) 30 seconds. For example, compositions can be resuspended in not more than 10, 15, 20, 15, 30, 35 or 40 seconds, preferably in NMT 30 seconds. In some embodiments, the compositions can be resuspended in not more than 15, 20, 25, 30, 40, 50, 60, 70, 80, 90, 100, 110, 120, 130, 140, 150, 160, 170, 180, 190, or about 200 seconds.

Syringeability and injectability are key-product performance parameters of any parenteral dosage form. As used herein, "syringeability" is determined by withdrawing the composition using a common syringe and needle type used for the administration of the pharmaceutically acceptable composition, for example from a vial and includes factors such as ease of withdrawal, clogging and accuracy of dose measurements. "Injectability" refers to the performance of the formulation during injection and includes pressure or force required for injection, evenness of flow, and freedom from clogging, for example no blockage of the needle. (Cilurzo, F, et al., Injectability Evaluation: An Open Issue. AAPS PharmSciTech. 2011 2: 604-609). Preferably, a 1 mL Luer Lock syringe with a 23 gauge, ⅜ inch safety needle is used to test syringeability. Compositions of the disclosure are syringeable and injectable, especially after resuspension by shaking.

As used herein, "osmolality" refers to the concentration of particles per kilogram of solution. It is expressed as mOsmol/kg and is measured using the standard method provided in USP<785>. (www.uspbpep.com/usp31/v31261/usp31nf26s1_c785.asp).

The compositions of the invention are both syringeable and injectable and are suited for subcutaneous administration, even after storage under stress conditions, for example, about 40° C./75% RH for 1 month or longer. To be suitable for subcutaneous administration after storage, the formulations must include 90% or more of API, e.g., MPA, as compared to the initial amount of API, after storage. To be suitable for subcutaneous administration after storage, the formulations must be resuspendable after no more than 30 seconds, after storage. To be suitable for subcutaneous administration after storage, the formulations must exhibit an osmolality of between 295 and 420, preferably 295 to 365 mOsm/kg. The compositions of the invention are syringeable and injectable and are suited for subcutaneous administration, even after storage at about 40° C./75% RH for 3 months or longer. The compositions of the invention are syringeable and injectable and are suited for subcutaneous administration, even after storage at about 40° C./75% RH for 6 months or longer. The compositions of the invention are syringeable and injectable and are suited for subcutaneous administration, even after storage at about 40° C./75% RH for 12 months or longer.

Specific embodiments of the present disclosure include

1. An aqueous composition for subcutaneous injection which includes medroxyprogesterone acetate at a concentration of about 260 mg/ml to 440 mg/ml, docusate sodium at a concentration of about 0.6 mg/ml to 1.5 mg/ml, and polyethylene glycol.

2. The composition of embodiment 1, wherein the concentration of polyethylene glycol is about 10 mg/ml to 40 mg/ml.

3. The composition of embodiment 1 or 2, wherein the concentration of polyethylene glycol is about 15 mg/ml to 30 mg/ml.

4. The composition of any one of embodiments 1 to 3, wherein the polyethylene glycol is polyethylene glycol 3350.

5. The composition of any one of embodiments 1 to 4, wherein the composition further includes a sulfate salt or a sodium salt or both a sulfate salt and a sodium salt.

6. The composition of embodiment 5, wherein the sulfate salt is sodium sulfate and the sodium salt is sodium chloride.

7. The composition of any one of embodiments 1 to 6, wherein the composition further includes a stabilizer.

8. The composition of embodiment 7, wherein the stabilizer is methionine.

9. The composition of embodiment 7, wherein the stabilizer is thioglycerol, monothioglycerol, lipoic acid, propyl gallate, cysteine, sodium formaldehyde sulfoxylate, or dihydrolipoic acid.

10. The composition of any one of embodiments 1 to 9, wherein the composition further comprises a buffering salt.

11. The composition of embodiment 10, wherein the buffering salt is a phosphate salt or a combination of phosphate salts.

12. The composition of embodiment 11, wherein the buffering salt is monobasic sodium phosphate, dibasic sodium phosphate, or a combination thereof.

13. The composition of any one of the preceding embodiments, in the form of a single unit dose.

14. The composition of any one of the preceding embodiments, having a pH of about 4.0 to about 7.0, or having a pH of about 6.0 to about 7.0.

15. The composition of any one of the preceding embodiments, having a pH of 6.0.

16. The composition of any one of the preceding embodiments, which further includes sodium sulfate, methionine, monobasic sodium phosphate, and dibasic sodium phosphate.

17. The composition of any one of the preceding embodiments, in the form of an aqueous suspension.

18. The composition of any one of the preceding embodiments, wherein the concentration of medroxyprogesterone acetate is about 400 mg/ml.

19. The composition of embodiment 18, wherein the concentration of docusate sodium is about 0.6 mg/ml.

20. The composition of embodiment 18, wherein the concentration of docusate sodium is about 1.3 mg/ml.

21. The composition of embodiment 18, wherein the concentration of docusate sodium is about 1.0 mg/ml.

22. The composition of any one of embodiments 19 to 21, wherein the concentration of polyethylene glycol is about 15 mg/ml to about 30 mg/ml.

23. The composition of any one of embodiments 19 to 22, wherein the concentration of polyethylene glycol is about 20 mg/ml.

24. The composition of any one of embodiments 19 to 22, wherein the concentration of polyethylene glycol is about 28 mg/ml.

25. The composition of any one of the preceding embodiments, wherein the medroxyprogesterone acetate is annealed.

26. The composition of any one of embodiments 1 to 17, wherein the concentration of medroxyprogesterone acetate is about 300 mg/ml.

27. The composition of embodiment 26, wherein the concentration of docusate sodium is about 0.6 mg/ml.

28. The composition of embodiment 26, wherein the concentration of docusate sodium is about 1.3 mg/ml.

29. The composition of embodiment 26, wherein the concentration of docusate sodium is about 1.0 mg/ml.

30. The composition of any one of embodiments 27 to 29, wherein the concentration of polyethylene glycol is about 15 mg/ml to about 30 mg/ml.

31. The composition of any one of embodiments 27 to 30, wherein the concentration of polyethylene glycol is about 20 mg/ml.

32. The composition of any one of embodiments 27 to 30, wherein the concentration of polyethylene glycol is about 28 mg/ml.

33. A method for preventing pregnancy or for treating endometriosis-associated pain, renal carcinoma, or endometrial carcinoma in a female patient which includes the step of subcutaneously administering to the patient a composition of any one of the preceding embodiments.

34. The method of embodiment 33, wherein the composition is administered once every four months.

35. The method of embodiment 33, wherein the composition is administered once every five months.

36. The method of embodiment 33, wherein the composition is administered once every six months.

The following examples are offered for illustrative purposes, and are not intended to limit the invention in any manner. Those of skill in the art will readily recognize a variety of noncritical parameters which can be changed or modified to yield essentially the same results.

EXAMPLES

Example 1: Medroxyprogesterone Acetate Compositions

The quantitative composition and function of each component in an exemplary embodiment of the disclosure is provided in Table 1.

TABLE 1

Unit composition in medroxyprogesterone acetate compositions

| Ingredients | Function of Components | Concentration (mg/mL) | Content (mg/vial) |
|---|---|---|---|
| Medroxyprogesterone Acetate, USP | Active Pharmaceutical Ingredient | 400 | 504 |
| Polyethylene glycol, 3350 USP/NF | Suspending Agent | 20.3 | 25.59 |
| Docusate sodium, USP/EP | Surfactant | 1.5 | 1.89 |
| Sodium sulfate anhydrous, USP/BP/Eur | Tonicity Adjuster | 11 | 13.86 |
| L-Methionine, USP/EP/JP | Stabilizer | 1.5 | 1.89 |
| Monobasic sodium phosphate, USP | Buffer | 0.25 | 0.32 |
| Dibasic Sodium phosphate, USP | Buffer | 0.52 | 0.66 |
| Water for Injection, USP | Vehicle | Q.S to 1 mL~1.07 g | Q.S to 1.26 mL |

Example 2: IID-Conforming Excipient Levels

All excipients except docusate sodium and sodium sulfate anhydrous fall below the inactive ingredient database (IID) limits for the intramuscular (IM) and subcutaneous (SC) routes of administration as supplied in the FDA IID database. IID limits for docusate sodium and sodium sulfate anhydrous are not available in FDA IID database. Separate non-clinical studies were performed to qualify these excipients for the subcutaneous route of administration.

TABLE 2

IID levels of the excipients used in the medroxyprogesterone acetate compositions

| Ingredients | IID Levels (%) (IM/SC Route of Administration) | Concentration (mg/mL) | % w/v |
|---|---|---|---|
| Polyethylene glycol, 3350 USP/NF* | 2.88 w/v | 20.3 | 2.03 |
| Docusate sodium, USP/EP | 0.015/NA | 1.5 | 0.15 |
| Sodium sulfate anhydrous, USP/BP/Eur | NA | 11 | 1.10 |
| L-Methionine, USP/EP/JP | 0.15 | 1.5 | 0.15 |
| Monobasic sodium phosphate, USP | 0.06 | 0.25 | 0.025 |
| Dibasic Sodium phosphate, USP | 0.07 | 0.52 | 0.052 |
| Sodium chloride | 1.23 for SC route 0.9 for IM/SC route | 4.5 | 0.45 |
| Water for Injection, USP | N/A | To 1 mL | To 1 mL |

*The FDA has determined a maximal concentration for injections in general of 6% w/v.

Example 3: Method of Manufacture

Compositions were prepared by dissolving all of the excipients in water for injection (WFI) and filtering the solution into another pre-sterilized tank. To this solution, dispensed medroxyprogesterone acetate was added in small increments with continuous mixing. The compounded bulk suspension was steam sterilized in the tank in the temperature range of 122° C. to 125° C. for a minimum of 15 minutes and a F0 value≥12 minutes. After steam sterilization, the bulk was cooled to room temperature. Prior to final weight make up with water for injection through a sterile filter, the pH of the suspension was measured and adjusted if needed with 0.1 N HCl or 0.1 N NaOH (through pH filter). The compounded and sterilized bulk suspension was aseptically filled into pre-sterilized and depyrogenated USP Type 1 glass vials and capped with pre-sterilized 13 mm rubber stopper and 13 mm flip-off aluminum seal. The entire batch of finished drug product underwent manual visual inspection for defects and then was stored in quarantine area until released.

Example 4: Stability Testing of Medroxyprogesterone Acetate Compositions

Various compositions were prepared and tested for stability. The components of those compositions are provided in Tables 3-6. PEG 3350 refers to polyethylene glycol, average MW 3350 g/Mol.

TABLE 3

Unit composition in medroxyprogesterone acetate (MPA) compositions tested for stability.

| INGREDIENTS | 96A mg/mL | 97A mg/mL | 98A mg/mL | 99A mg/mL | 138A mg/mL |
|---|---|---|---|---|---|
| MPA | 400 | 400 | 400 | 400 | — |
| MPA, annealed | — | — | — | — | 400 |
| PEG 3350 | 20.00 | 28.00 | 20.00 | 20.00 | 20.00 |
| Docusate sodium | 0.60 | 1.30 | 1.30 | 1.00 | 1.00 |
| Sodium Sulfate, anh. | 12.00 | 11.00 | 13.00 | 13.00 | 13.00 |
| L-Methionine | 1.50 | 1.50 | 1.50 | 1.50 | 1.50 |
| Dibasic sodium phosphate, anh. | 0.23 | 0.23 | 0.23 | 0.23 | 0.23 |
| Monobasic sodium phosphate, anh. | 0.60 | 0.60 | 0.60 | 0.60 | 0.60 |
| WFI | q.s. to 1 mL | q.s. to 1 mL | q.s. to 1 mL | q.s. to 1 mL | q.s. to 1 mL |

TABLE 4

Unit composition in medroxyprogesterone acetate compositions tested for stability

| INGREDIENTS | 132A mg/mL | 133A mg/mL | 134A mg/mL | 135A mg/mL |
|---|---|---|---|---|
| MPA | 300 | 300 | 300 | 300 |
| PEG 3350 | 20.00 | 20.00 | 20.00 | 20.00 |
| Docusate sodium | 0.60 | 0.60 | 1.00 | 1.00 |
| Sodium Sulfate, anh. | 13.00 | 10.00 | 13.00 | 10.00 |
| L-Methionine | 1.50 | 1.50 | 1.50 | 1.50 |
| Dibasic sodium phosphate, anh. | 0.23 | 0.23 | 0.23 | 0.23 |
| Monobasic sodium phosphate, anh. | 0.60 | 0.60 | 0.60 | 0.60 |
| WFI | q.s. to 1 mL | q.s. to 1 mL | q.s. to 1 mL | q.s. to 1 mL |

TABLE 5

Unit composition in medroxyprogesterone acetate compositions tested for stability

| INGREDIENTS | 201 mg/mL | 202 mg/mL | 203 mg/mL | 204 mg/mL | 205 mg/mL | 206 mg/mL |
|---|---|---|---|---|---|---|
| MPA | 400 | 400 | 400 | 400 | 400 | 400 |
| PEG 3350 | 15,00 | 30,00 | 15,00 | 30,00 | 15,00 | 30,00 |
| Docusate sodium | 0,60 | 0,60 | 1,00 | 1,00 | 1,30 | 1,30 |
| Sodium Sulfate, anh. | 13,00 | 10,00 | 13,00 | 10,00 | 13,00 | 10,00 |
| L-Methionine | 1,50 | 1,50 | 1,50 | 1,50 | 1,50 | 1,50 |
| Dibasic sodium phosphate, anh. | 0,23 | 0,23 | 0,23 | 0,23 | 0,23 | 0,23 |
| Monobasic sodium phosphate, anh. | 0,60 | 0,60 | 0,60 | 0,60 | 0,60 | 0,60 |
| WFI | q.s. to 1 mL | q.s. to 1 mL | q.s. to 1 mL | q.s. to 1 mL | q.s. to 1 mL | q.s. to 1 mL |

TABLE 6

Unit composition in medroxyprogesterone acetate compositions tested for stability

| INGREDIENTS | 236 mg/mL | 237 mg/mL | 238 mg/mL | 239 mg/mL | 240 mg/mL | 241 mg/mL |
|---|---|---|---|---|---|---|
| MPA | 300 | 300 | 300 | 300 | 300 | 300 |
| PEG 3350 | 15,00 | 30,00 | 15,00 | 30,00 | 15,00 | 30,00 |
| Docusate sodium | 0,60 | 0,60 | 1,00 | 1,00 | 1,30 | 1,30 |
| Sodium Sulfate, anh. | 13,00 | 10,00 | 13,00 | 10,00 | 13,00 | 10,00 |
| L-Methionine | 1,50 | 1,50 | 1,50 | 1,50 | 1,50 | 1,50 |
| Dibasic sodium phosphate, anh. | 0,23 | 0,23 | 0,23 | 0,23 | 0,23 | 0,23 |
| Monobasic sodium phosphate, anh. | 0,60 | 0,60 | 0,60 | 0,60 | 0,60 | 0,60 |
| WFI | q.s. to 1 mL | q.s. to 1 mL | q.s. to 1 mL | q.s. to 1 mL | q.s. to 1 mL | q.s. to 1 mL |

The drug product was filled into Uniject™ containers and exposed to different storage conditions, including variations in temperature, and relative humidity, for up to 60 months. The Uniject™ containers were tested during the course of the storage period for, e.g., physical appearance, impurity/degradation products, pH, assay, particle size, resuspendability, syringeability, content uniformity of the delivered dose, sedimentation volume—cylinder, osmolality and Zeta potential.

Assessing the physical appearance and description of the product comprised providing (1) a description of the product, (2) assessing container closure integrity, and (3) assessing resuspendability.

Suitable test specimens matched the following description: white particles in suspension and free from visible extraneous contamination.

Resuspendability was assessed by dispersing the product by shaking for a period of time and comparing to the description of the product. If the appearance matches the description with no signs of caking or agglomerated particles, it is suitable for use. Shaking time for achieving product description was noted. In preferred embodiments, the compositions resuspend in not more than 30 sec.

Obtaining an "assay" of the product comprised calculating the amount of medroxyprogesterone acetate in the composition as a percent of the label claim (e.g. 300 mg/ml or 400 mg/ml) following the HPLC protocol detailed in Example 5.

Zeta potential, surface charge, of the particles was measured using a Zetasizer instrument (Malvern UK) in 10 mM solution of NaCl.

An assessment of impurity/degradation products was obtained by following the HPLC protocol described in Example 7.

Particle size distribution, or PSD, was calculated by following the protocol described in Example 8.

Viscosity may be calculated by following the protocol described in Example 9.

Example 5: HPLC Protocol for Calculating the Amount of Medroxyprogesterone Acetate in the Composition Equipment: Suitable UPLC pump capable of pumping at approximately 0.4 mL/minute; suitable UV—wavelength spectrophotometric detector or photodiode array (PDA) detector; Waters Acquity UPLC BEH C18, 2.1-mm (i.d.)× 100-mm, 1.7 µm particle size; suitable injection system; suitable data acquisition system; and suitable column oven.

Reagents: Acetonitrile, HPLC grade; formic acid, HPLC grade; and water, grade suitable for chromatographic analysis.

Chromatographic parameters are as follows:

TABLE 7

Chromatographic parameters

| | |
|---|---|
| Flow Rate | 0.4 mL/minute |
| Detector | 245 nm (PDA: 190-400 nm, for ID only) |
| Injection Volume | 2.0 µL |
| Column Set Temperature | 55° C. |
| Run Time | 20.0 min |
| Needle Wash | ACN |
| Initial Pressure | 6000-8000 psi |

The parameters may be adjusted to achieve the proper chromatography: flow rate, detector sensitivity, mobile phase proportions (not composition), column dimensions and particle size. The gradient table is as follows:

TABLE 8

Gradient table

| Time (min) | Mobile Phase A (%) | Mobile Phase B (%) |
|---|---|---|
| 0.0 | 57.0 | 43.0 |
| 11.0 | 57.0 | 43.0 |
| 11.5 | 5.0 | 95.0 |
| 14.5 | 5.0 | 95.0 |
| 15.0 | 57.0 | 43.0 |
| 20.0 | 57.0 | 43.0 |

Preparation of the mobile phase A was achieved by adding 1 mL of formic acid to 1000 mL of water in a suitable container and mixing well then filtering the solution through a 0.2-µm nylon membrane filter, mixing well and labeling.

Preparation of the mobile phase B was achieved by using acetonitrile, filtering through a 0.2-µm nylon membrane filter, mixing well and labeling.

Preparation of the diluent was achieved by combining 500 mL of water and 500 mL of acetonitrile, mixing well, filtering through a 0.2-µm nylon membrane filter, mixing well and labeling.

Preparation of the standard solution was achieved by weighing accurately about 10 mg of medroxyprogesterone acetate reference standard into a 20-mL volumetric flask, adding approximately 18 mL of Diluent, mixing and sonicating to dissolve if necessary, allowing to cool to room temperature, diluting to volume with Diluent, mixing well and labeling.

Preparation of the resolution solution was achieved by weighing approximately 5.0 mg of medroxyprogesterone acetate for system suitability CRS into a 10-mL volumetric flask, adding approximately 7.5 mL of diluent, mixing and sonicating to dissolve if necessary, diluting to volume with diluent, mixing well and labeling.

Preparation of the sample solution was achieved by resuspending the product by vigorously shaking Uniject™ containers until complete resuspension before use and transferring the content of appropriate number of Uniject™ containers into one container. The next step was pipetting with TC pipette homogenized suspension into adequate volumetric flask. The next step was rinsing the TC pipette with diluent and making sure no suspension is remaining in the pipette. The next step was making appropriate dilutions with diluent to reach a final sample concentration of 0.4 to 0.6 mg/mL, sonicating if necessary, to dissolve all solids during dilution, allowing cooling to room temperature after sonication.

Those of skill in the art will readily appreciate that weights and volumes described herein may be adjusted, so long as the initial and final concentrations are the same.

To obtain the chromatograph, the diluent was injected, and then the resolution solution and standard solution were injected, and peak areas recorded. Once the system suitability requirements were met, the standard and sample solutions were injected following current procedures. Finally, the amount of medroxyprogesterone acetate is calculated using standard algorithms known to those in the art.

Example 6: HPLC Protocol for Determining Composition Dissolution

Equipment: same as for Example 5, supra.
Reagents: Acetonitrile, HPLC grade; formic acid, Sodium Dodecylsulfate; and water, grade suitable for chromatographic analysis.

Chromatographic parameters are as follows:

TABLE 9

Chromatographic parameters

| | |
|---|---|
| Flow Rate | 0.4 mL/minute |
| Detector | 245 nm (PDA: 190-400 nm, for ID only) |
| Injection Volume | 2.0 µL |
| Column Set Temperature | 55° C. |
| Run Time | About 5 minutes |
| Needle Wash | Diluent |

The dissolution parameters are as follows:

TABLE 10

Dissolution parameters

| | |
|---|---|
| Apparatus | USP Apparatus 2 (paddles) |
| Rotation Speed | 50 rpm |
| Dissolution Medium | 0.5% SDS in water |
| Volume | 900 mL |
| Temperature | 37 ± 0.5° C. |
| Distance from bottom | 2.5 cm |
| Time points | 30 min |

Preparation of the mobile phase is achieved by combining 1000 mL of water and 1000 mL of acetonitrile, mixing well, filtering through a 0.2-µm nylon membrane filter, mixing well and labeling.

Preparation of the dissolution medium is achieved by weighing about 30 g of SDS, transferring the SDS into a 6 L flask, adding approximately 5 L of water, stirring until dissolved, diluting to 6 L with water, mixing well and labeling. The dissolution medium is used as the diluent.

Preparation of the standard solution is achieved by weighing accurately about 22 mg of medroxyprogesterone acetate reference standard into a 100-mL volumetric flask, adding approximately 5 mL of diluent, mixing and sonicating to dissolve if necessary, allowing to cool to room temperature, diluting to volume with diluent, mixing well and labeling. Those of skill in the art will readily appreciate that weights and volumes can be adjusted, provided the concentration of the standard solution is the same.

Preparation of the sample solution is achieved by manually withdrawing an appropriate volume of the sample solution at each time point, centrifuging the sample solution at 3,000 rpm for about 5 minutes and using the supernatant for analysis.

To obtain the chromatograph, the diluent is injected, and then the resolution solution and standard solution are injected, and peak areas are recorded. Once the system suitability requirements have been met, the standard and sample solutions are injected following current procedures. Finally, the percent release is calculated using standard algorithms known to those in the art.

Example 7: HPLC Protocol for Determining the Amount of Impurities/Degradation Products Equipment: Suitable UPLC pump capable of pumping at approximately 0.4 mL/minute; suitable UV—wavelength spectrophotometric detector or photodiode array (PDA) detector; Waters Acquity UPLC BEH C18, 2.1-mm (i.d.)× 100-mm, 1.7 µm particle size; suitable injection system; suitable data acquisition system; and suitable column oven.

Reagents: Acetonitrile, HPLC grade; formic acid, HPLC grade; tetrahydrofuran (THF), HPLC grade; and water, grade suitable for chromatographic analysis.

Chromatographic parameters are as follows:

TABLE 11

Chromotographic parameters

| | |
|---|---|
| Flow Rate | 0.4 mL/minute |
| Detector | 245 nm (PDA: 190-400 nm, for ID only) |
| Injection Volume | 5.0 µL |
| Column Set Temperature | 55° C. |
| Run Time | 30.0 min |
| Needle Wash | ACN |
| Initial Pressure | 6000-8000 psi |

The parameters may be adjusted to achieve the proper chromatography: flow rate, detector sensitivity, mobile phase proportions (not composition), column dimensions and particle size. The gradient table is as follows:

TABLE 12

Gradient table

| Time (min) | Mobile Phase A (%) | Mobile Phase B (%) |
|---|---|---|
| 0.0 | 80.0 | 20.0 |
| 10.0 | 70.0 | 30.0 |
| 22.0 | 70.0 | 30.0 |
| 22.1 | 5.0 | 95.0 |
| 25.0 | 5.0 | 95.0 |
| 25.1 | 80.0 | 20.0 |
| 30.0 | 80.0 | 20.0 |

Preparation of the mobile phase A was achieved by adding 1 mL of formic acid to 1000 mL of water in a suitable container and mixing well then filtering the solution through a 0.2-µm nylon membrane filter, mixing well and labeling.

Preparation of the mobile phase B was achieved by combining acetonitrile and THF in a ratio of 65:35, filtering through a 0.2-µm nylon membrane filter, mixing well and labeling.

Preparation of the diluent was achieved by combining 500 mL of water and 500 mL of acetonitrile, mixing well, filtering through a 0.2-µm nylon membrane filter, mixing well and labeling.

Preparation of the stock standard solution was achieved by weighing accurately about 10 mg of medroxyprogesterone acetate reference standard into a 20-mL volumetric flask, adding approximately 18 mL of diluent, mixing and sonicating to dissolve if necessary, allowing to cool to room temperature, diluting to volume with diluent, mixing well and labeling.

Preparation of the standard solution was achieved by pipetting 1.0 mL of the stock standard solution into a 200-mL volumetric flask, diluting to volume with diluent, mixing well and labeling.

Preparation of the resolution solution was achieved by weighing approximately 5.0 mg of medroxyprogesterone acetate for system suitability CRS into a 10-mL volumetric flask, adding approximately 7.5 mL of diluent, mixing and sonicating to dissolve if necessary, diluting to volume with Diluent, mixing well and labeling.

Preparation of the quantitation limit solution was achieved by pipetting 5.0 mL of the standard solution into a 50-mL volumetric flask, diluting to volume with diluent, mixing well and labeling.

Preparation of the sample solution was achieved by resuspending the product by vigorously shaking Uniject™ containers until complete resuspension before use and transferring the content of appropriate number of Uniject™ containers into one container. The next step was pipetting with TC pipette homogenized suspension into adequate volumetric flask. The next step was completely rinsing the TC pipette with Diluent. The next step was making appropriate dilutions with diluent to reach a final sample concentration of 0.4 to 0.6 mg/mL, sonicating if necessary, to dissolve all solids during dilution, allowing cooling to room temperature after sonication.

Those of skill in the art will readily appreciate that weights and volumes described herein may be adjusted, so long as the initial and final concentrations are the same.

To obtain the chromatograph, the diluent is injected, and then the quantitation limit solution, resolution solution and standard solution are injected, and peak areas are recorded. Once the system suitability requirements have been met, the standard and sample solutions are injected following current procedures. Finally, the amount of impurities/degradation products present in a sample is calculated using standard algorithms known to those in the art.

Example 8: Protocol for Measuring Particle Size in the Composition

Equipment: Malvern laser diffraction Mastersizer 3000 or equivalent and measuring cell (HydroMV or equivalent).

Reagents: water, suitable for analytical analysis and polysorbate 80.

TABLE 13

Parameters

| | |
|---|---|
| Particle RI | 1.536 (also for blue light) |
| Absorption | 0.01 (also for blue light) |
| Dispersant | 0.05% polysorbate 80 in water |
| Dispersant RI | 1.33 |
| Particle Shape | Non-spherical |
| Blue light | Enabled |
| Measuring time | 10 seconds |
| Background measuring time | 10 seconds |
| Measurements | 3 |
| Obscuration | 7-12% |
| Speed rate of the flow cell | 1500 rpm |
| Sonication | 30 seconds |
| Sonication power | 50% |
| Premeasurement delay | 10 seconds |
| Analysis model | General purpose |
| Result type | Volume distribution |

The dispersants were prepared by weighing about 2 g polysorbate 80 in a 200-mL volumetric flask, diluting to volume with water, mixing well and labeling as polysorbate 80 stock. The concentration of polysorbate 80 is 1%. Next, 10 mL of Polysorbate 80 Stock was pipetted into a 2000-mL volumetric flask, diluted to volume with water, mixed well and labeled. The concentration of polysorbate 80 was 0.005%.

The cell was cleaned before starting measurement and between runs with degassed water.

The background measurement was taken by filling the measuring cell with dispersant, starting recirculation, and starting the background measurements.

The sample measurement was taken by resuspending the sample dispersion by vigorously shaking for not less than 20 seconds before use. The next step was slowly adding drop wise to the measuring cell filled with dispersant, until an obscuration of 7-12% is reached, then starting sonication for 30 sec at power of 50%, allowing the sample to stir about 10 seconds at 1500 rpm, and starting the measurement. If the weighted residual is greater than 3%, repeat the experiment.

Example 9: Protocol for Measuring Viscosity

Equipment: Brookfield Viscometer DV-II+ PRO, or equivalent and cone spindle CPE-40, CPA-40Z or equivalent.

Reagents: Brookfield viscosity general purpose silicone fluid, 10 cP at 25° C.

Measurement conditions: volume of 0.5 mL, spindle speed of 12 rpm and temperature of 25° C.

To time the use performance check, the viscometer is auto zeroed, the spindle is selected and the electronic gap is set. With the viscometer stopped, the sample cup is removed and 0.5 mL of a 10 cP Brookfield viscosity standard is pipetted into the cup. The sample cup is connected to the viscometer and sufficient time is allowed for the temperature to reach equilibrium. A viscometer speed is selected and the spindle is rotated. The temperature, spindle speed and viscosity are recorded. The instrument and viscosity standard fluid error are combined to calculate the total allowable error using calculations known to one of skill in the art.

Other instrumentation, for example, an Anton Paar Rheometer, can also be used to measure viscosity, using techniques and methods known in the art.

Example 10: Local Tolerance Studies

Initial selection of medroxyprogesterone injectable suspension at 300 mg/mL with Polysorbate 80 and medroxyprogesterone acetate injectable suspension at 400 mg/mL was based on plasma exposure and tolerability data collected from an ongoing non-good laboratory practice (GLP) pharmacokinetic and tolerability study in New Zealand White (NZW) rabbits. In this study 6 groups of 5 female NZW rabbits received a single subcutaneous administration of MPA in different formulations into the scapular region. Group 1 animals received injection of Depo-SubQ Provera 104, the listed drug, and a second administration after 3 months, resulting in all animals receiving a total dose of 208 mg. Groups 2, 3, and 5 were terminated after 3 months and groups 1, 4, and 6 will be followed for 1 year.

A summary of the non-GLP exploratory rabbit pharmacokinetic study with data up to study day 239 is provided in Table 14.

TABLE 14

Non-GLP Exploratory Rabbit Pharmacokinetic Study

| Group No. | Formulation | Dose route | Target dose volume (mL/animal) | Target dose level (mg/animal/ dose) | Nominal conc. (mg/mL) | Mean MPA average plasma conc. (ng/mL) |
|---|---|---|---|---|---|---|
| 1 | Depo-SubQ Provera 104 ® | SC | 0.65 | 104 | 160 | 4.13 (22.0) |
| 2 | MPA in docusate sodium | SC | 1.39 | 208 | 150 | 4.41 (13.4) |
| 3 | MPA in polysorbate 80 | SC | 1.39 | 208 | 150 | 2.99 (18.2) |
| 4 | MPA in polysorbate 80 | SC | 0.69 | 208 | 300 | 3.15 (8.9) |
| 5 | Unmilled MPA in docusate sodium | SC | 0.52 | 208 | 400 | 3.39 (37.8) |
| 6 | MPA in docusate sodium (formulation in Table 1) | SC | 0.52 | 208 | 400 | 2.93 (39.9) |

Figure 2:
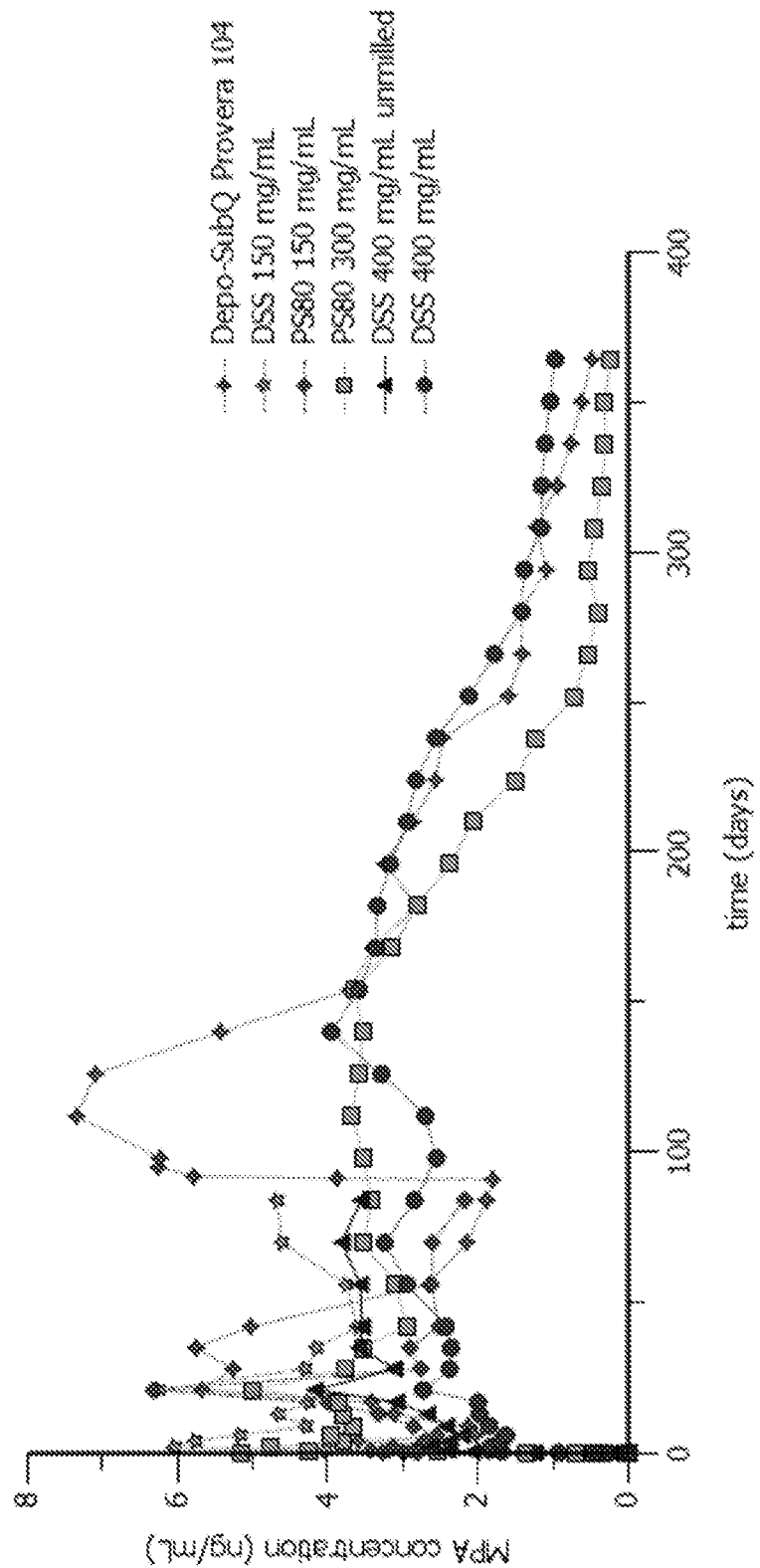
FIG. 2 depicts mean plasma concentration time profiles of medroxyprogesterone acetate in rabbits up to day 365 postdose.
Figure 3:
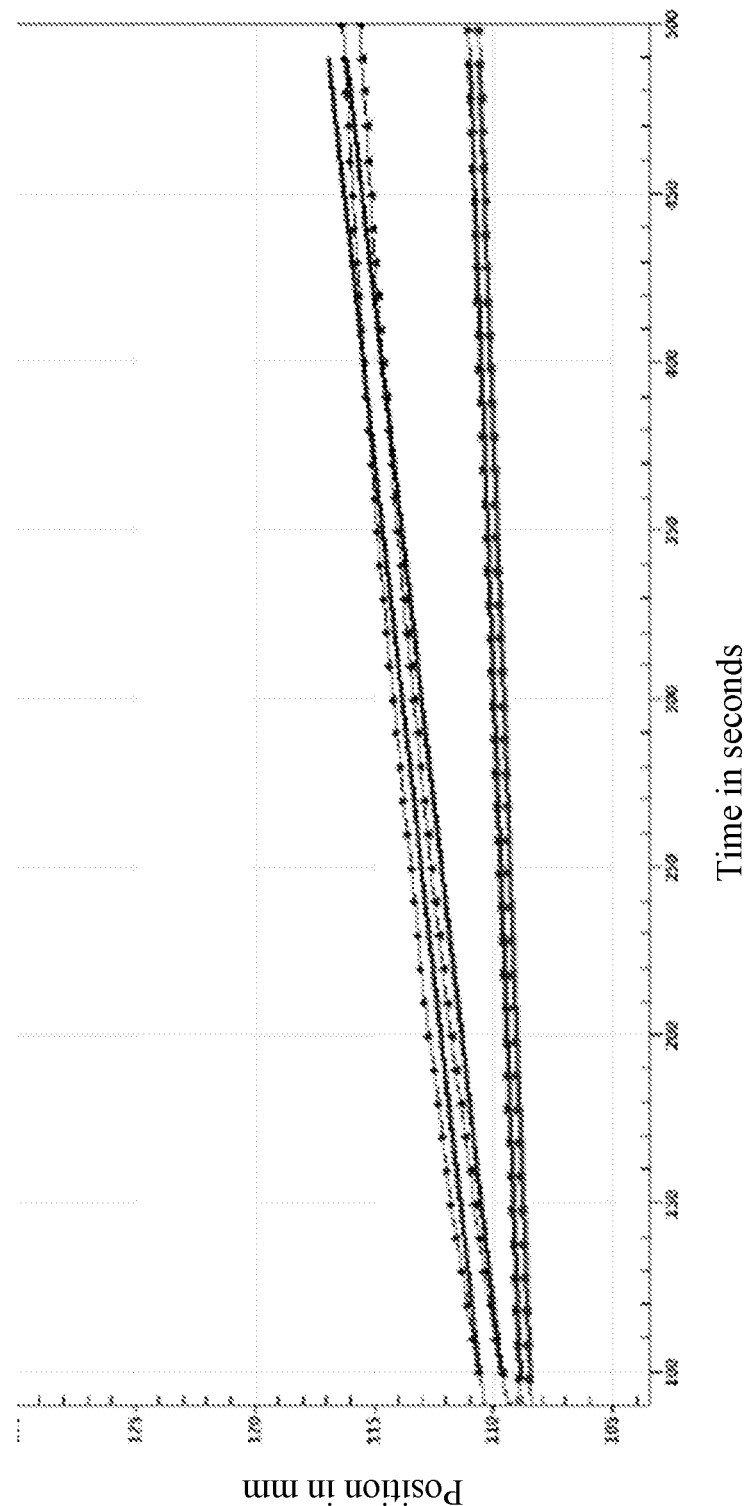
FIG. 3 is a plot of sedimentation rate (position in mm on the y-axis as a function of time in seconds on the x-axis), where the top two lines (plotted as circles and upright triangles) represent formulations with 400 mg/ml medroxyprogesterone acetate with a d(90) of 30 μm and where the bottom two lines (plotted as squares and downward-pointing triangles) represent formulations with 400 mg/ml medroxyprogesterone acetate with a d(90) of 9 μm.

Preliminary results obtained from the non-GLP pharmacokinetic study in NZW rabbits did not display a significant burst-effect in rabbits (FIG. 1). Generally, mean steady-state MPA plasma levels were reached within 12 to 24 hours postdose and were similar compared to the listed drug (FIG. 2). The 2-fold higher single dose of MPA in the test formulations (groups 2 to 6) did not result in higher plasma concentrations. PK measurement of formulations 2, 3, and 5 was stopped after 3 months while PK after injection of formulations 1 (Dep-SubQ Provera 104® two injections), 4 (300 mg/M: MPA and polysorbate) and 6 (400 mg/ml MPA and 1.5 mg/ml docusate sodium) was followed for one year.

The plasma concentration-time profiles of the test formulations 2-6 were generally similar up to day 85 compared to the listed drug (Depo-SubQ Provera 104) despite the 2-fold higher dose administered in the test formulations (FIG. 2). A burst was not observed. On study day 365 MPA concentrations >0.5 ng/mL were still present in 1 of 4 surviving animals in groups 1 (Depo-SubQ Provera 104) and 4 (polysorbate 80), and in 3 of 5 animals from group 6, indicating the longest sustained MPA exposure for the formulation comprising 400 mg/ml MPA and 1.5 mg/ml docusate sodium.

Upon gross tissue assessment of the injection site, only slight edema (grade 1) was noted 2 to 4 hours dose in 1 or 2 rabbits in all test formulation-treated groups; and no gross tissue abnormalities were noted on day 2 postdose and thereafter (up to day 29, when formal injection site scoring was discontinued). There were only minimal (non-statistically significant) differences noted in hematology and clinical pathology.

Based on this data and preliminary stability data, the safety of both medroxyprogesterone formulations was assessed as follows. The medroxyprogesterone acetate composition with DSS was evaluated in a 9-month GLP rabbit local tolerance study. Also evaluated in the study was a less stable medroxyprogesterone acetate composition at 300 mg/mL containing polysorbate 80. The two formulations were composed of different excipients and different concentrations of medroxyprogesterone acetate, but the overall dose was fixed by injecting a smaller volume for the claimed composition, which had the more concentrated MPA. A group of rabbits assigned to this trial received the referenced marketed comparator, Depo-SubQ Provera 104®.

The study design is summarized in Table 15, below.

TABLE 15

Experimental design of a 9-month GLP local tolerance investigation in female rabbits

| Group No. | Test material | Dose level (mg) | Dose concentration (mg/mL) | Dose volume (mL) | No. of females assigned |
|---|---|---|---|---|---|
| 1 | 0.9% Sodium chloride for injection | 0 | 0 | 1 | 12 |
| 2 | Depo-SubQ Provera 104 ® | 104 | 160 | 0.65 | 12 |
| 3 | Placebo of injectable suspension, 300 mg/mL with 3.0 mg/mL of polysorbate 80 | 0 | 0 | 1 | 12 |
| 4 | MPA injectable suspension, 300 mg/mL with 3.0 mg/mL of polysorbate 80 | 300 | 300 | 1 | 12 |
| 5 | Placebo of injection suspension, 400 mg/mL with DSS at 1.5 mg/mL | 0 | 0 | 0.75 | 12 |
| 6 | MPA injection suspension, 400 mg/mL with DSS at 1.5 mg/mL (formulation in TABLE 1) | 300 | 400 | 0.75 | 12 |

The listed drug (group 2) was subcutaneously dosed on day 1, and a second dose of the listed drug occurred on day 90, while groups receiving saline control, vehicle control, or experimental formulations were dosed just on day 1. The highest dose level administered in the study was 300 mg. Rabbits were assessed for signs of clinical abnormalities. In addition, at day 7 and month 3, rabbits were euthanized humanely, and the following tissues were microscopically assessed: injection site with associated regional draining lymph nodes (interscapular and axillary), liver, ovaries, uterus, adrenal glands, and any abnormal-appearing tissues. All other collected tissues were stored in fixative. The same necropsy/organ collection/microscopic assessment procedure occurs during months 6 and 9.

Full clinical pathology parameters (hematology, clinical biochemistry, coagulation panel, and urinalysis) were assessed and conventional microscopic pathology assessments to determine organ/tissue/cellular alterations are included. Furthermore, plasma toxicokinetics samples were collected at predose, and at 6, 24 (study day 2), and 48 (study day 3) hours postdose and on study day 7, 14, 30, 60, 90, 120, 150, 180, and 270 and assayed using a validated bioanalytical assay.

Observations made during the 7-day interim necropsy time point noted the aqueous (vehicle) component of both formulations to be completely absorbed from the site of injection and only a white, flat, solid cake-like substance (same color of MPA) remained at the site of injection. These observations concluded that the vehicle component of the DSS-containing formulation was acutely absorbed into systemic circulation. The study termination time points are provided in Table 16.

TABLE 16

Rabbit study termination time points

| Group No. | Test material | Dose level (mg) | Number of females required per interim and terminal euthanasia time point | | | |
|---|---|---|---|---|---|---|
| | | | 7-day | 3-mo. | 6-mo. | 9-mo. |
| 1 | 0.9% Sodium chloride for injection | 0 | 3 | 3 | 3 | 3 |
| 2 | Depo-SubQ Provera 104 ® | 104 | 3 | 3 | 3 | 3 |
| 3 | Placebo of injectable suspension, 300 mg/mL with 3.0 mg/mL of polysorbate 80 | 0 | 3 | 3 | 3 | 3 |
| 4 | MPA injectable suspension, 300 mg/mL with 3.0 mg/mL of polysorbate 80 | 300 | 3 | 3 | 3 | 3 |
| 5 | Placebo of injection suspension, 400 mg/mL with DSS at 1.5 mg/mL | 0 | 3 | 3 | 3 | 3 |
| 6 | MPA injection suspension, 400 mg/mL with DSS at 1.5 mg/mL (formulation in Table 1) | 300 | 400 | 0.75 | 12 | |

Example 11: Medroxyprogesterone Acetate Compositions [039, 112]

The quantitative composition and function of each component in an exemplary embodiment of the disclosure is provided in Table 17.

TABLE 17

Unit composition in medroxyprogesterone acetate compositions

| Ingredients | Function of Components | Concentration (mg/mL) | Content (mg/vial) |
|---|---|---|---|
| MPA, USP | API | 200 | 252 |
| Polyethylene glycol 3350 NF | Suspending Agent | 20.3 | 25.58 |
| Docusate sodium, USP | Surfactant | 1.5 | 1.89 |
| Sodium sulfate anhydrous, USP | Tonicity Adjuster | 11 | 13.86 |
| L-Methionine, USP | Stabilizer | 1.5 | 1.89 |
| Monobasic sodium phosphate, Anhydrous, USP | Buffer | 0.25 | 0.32 |
| Dibasic Sodium phosphate Anhydrous, USP | Buffer | 0.52 | 0.66 |
| Water for Injection, USP | Vehicle | Q.S to 1 mL | Q.S to 1.26 mL |

Example 12: Medroxyprogesterone Acetate Compositions

The quantitative composition and function of each component in an exemplary embodiment of the disclosure is provided in Table 18.

TABLE 18

Unit composition in medroxyprogesterone acetate compositions

| Ingredients | Function of Components | Concentration (mg/mL) | Content (mg/vial) |
|---|---|---|---|
| MPA, USP | API | 150 | 189 |
| Polyethylene glycol 3350 NF | Suspending Agent | 20.3 | 25.58 |
| Docusate sodium USP | Surfactant | 1.5 | 1.89 |
| Sodium sulfate anhydrous, USP | Tonicity Adjuster | 11 | 13.86 |
| L-Methionine, USP | Stabilizer | 1.5 | 1.89 |
| Monobasic sodium phosphate, Anhydrous, USP | Buffer | 0.25 | 0.32 |
| Dibasic Sodium phosphate Anhydrous, USP | Buffer | 0.52 | 0.66 |
| Water for Injection, USP | Vehicle | Q.S to 1 mL | Q.S to 1.26 mL |

Example 13: Medroxyprogesterone Acetate Compositions

The quantitative composition and function of each component in an exemplary embodiment of the disclosure is provided in Table 19.

TABLE 19

Unit composition in medroxyprogesterone acetate compositions

| Ingredients | Function of Components | Concentration (mg/mL) | Content (mg/vial) |
|---|---|---|---|
| MPA, USP | API | 200 | 252 |
| Polyethylene glycol 3350 NF | Suspending Agent | 10.15 | 12.789 |
| Docusate sodium, USP | Surfactant | 0.75 | 0.945 |
| Sodium chloride | Tonicity Adjuster | 4.5 | 5.67 |
| Sodium sulfate anhydrous, USP | Tonicity Adjuster | 5.5 | 6.93 |
| L-Methionine, USP | Stabilizer | 0.75 | 0.945 |
| Monobasic sodium phosphate, Anhydrous, USP | Buffer | 0.125 | 0.1575 |
| Dibasic Sodium phosphate Anh, USP | Buffer | 0.26 | 0.3276 |
| Water for Injection, USP | Vehicle | Q.S to 1 mL | Q.S to 1.26 mL |

Example 14: Medroxyprogesterone Acetate Compositions

The quantitative composition and function of each component in an exemplary embodiment of the disclosure is provided in Table 20.

TABLE 20

Unit composition in medroxyprogesterone acetate compositions

| Ingredients | Function of Components | Concentration (mg/mL) | Content (mg/vial) |
|---|---|---|---|
| MPA, USP | API | 400 | 504 |
| Polyethylene glycol 3350 NF | Suspending Agent | 25 | 31.5 |
| Docusate sodium, USP | Surfactant | 2.1 | 2.646 |
| Sodium sulfate anhydrous, USP | Tonicity Adjuster | 11 | 13.86 |
| L-Methionine, USP | Stabilizer | 1.5 | 1.89 |
| Monobasic sodium phosphate, Anhydrous, USP | Buffer | 0.25 | 0.32 |
| Dibasic Sodium phosphate Anhydrous, USP | Buffer | 0.52 | 0.66 |
| Water for Injection, USP | Vehicle | Q.S to 1 mL | Q.S to 1.26 mL |

Example 15: Medroxyprogesterone Acetate Compositions

The quantitative composition and function of each component in an exemplary embodiment of the disclosure is provided in Table 21.

TABLE 21

Unit composition in medroxyprogesterone acetate compositions

| Ingredients | Function of Components | Concentration (mg/mL) | Content (mg/vial) |
|---|---|---|---|
| MPA, USP | API | 200 | 252 |
| Polyethylene glycol 3350 NF | Suspending Agent | 25 | 31.5 |
| Docusate sodium, USP | Surfactant | 2.1 | 2.646 |
| Sodium sulfate anhydrous, USP | Tonicity Adjuster | 11 | 13.86 |
| L-Methionine, USP | Stabilizer | 1.5 | 1.89 |
| Monobasic sodium phosphate, Anhydrous, USP | Buffer | 0.25 | 0.32 |
| Dibasic Sodium phosphate Anhydrous, USP | Buffer | 0.52 | 0.66 |
| Water for Injection, USP | Vehicle | Q.S to 1 mL | Q.S to 1.26 mL |

Example 16: Medroxyprogesterone Acetate Compositions

The quantitative composition and function of each component in an exemplary embodiment of the disclosure is provided in Table 22.

TABLE 22

Unit composition in medroxyprogesterone acetate compositions

| Ingredients | Function of Components | Concentration (mg/mL) |
|---|---|---|
| MPA, USP | API | 400 |
| Polyethylene glycol 3350 NF | Suspending Agent | 10-40 |
| Docusate sodium, USP | Surfactant | 0.6-1.5 |
| Sodium sulfate anhydrous, USP | Tonicity Adjuster | 10-15 |
| L-Methionine, USP | Stabilizer | 1.5 |
| Monobasic sodium phosphate, Anhydrous, USP | Buffer | ≥0.6 |
| Dibasic Sodium phosphate Anhydrous, USP | Buffer | ≥0.23 |
| Water for Injection, USP | Vehicle | Q.S to 1 mL |

Example 17: Medroxyprogesterone Acetate Compositions

The quantitative composition and function of each component in an exemplary embodiment of the disclosure is provided in Table 23.

TABLE 23

Unit composition in medroxyprogesterone acetate compositions

| Ingredients | Function of Components | Concentration (mg/mL) |
|---|---|---|
| MPA, USP | API | 400 |
| Polyethylene glycol 3350 NF | Suspending Agent | 15-30 |
| Docusate sodium, USP | Surfactant | 0.6-1.5 |
| Sodium sulfate anhydrous, USP | Tonicity Adjuster | 10-13 |
| L-Methionine, USP | Stabilizer | 1.5 |
| Monobasic sodium phosphate, Anhydrous, USP | Buffer | ≥0.6 |
| Dibasic Sodium phosphate Anhydrous, USP | Buffer | ≥0.23 |
| Water for Injection, USP | Vehicle | Q.S to 1 mL |

Example 18: Medroxyprogesterone Acetate Compositions

The quantitative composition and function of each component in an exemplary embodiment of the disclosure is provided in Table 24.

TABLE 24

Unit composition in medroxyprogesterone acetate compositions

| Ingredients | Function of Components | Concentration (mg/mL) |
|---|---|---|
| MPA, USP | API | 300 |
| Polyethylene glycol 3350 NF | Suspending Agent | 10-40 |
| Docusate sodium, USP | Surfactant | 0.6-1.5 |
| Sodium sulfate anhydrous, USP | Tonicity Adjuster | 10-15 |
| L-Methionine, USP | Stabilizer | 1.5 |
| Monobasic sodium phosphate, Anhydrous, USP | Buffer | ≥0.6 |
| Dibasic Sodium phosphate Anhydrous, USP | Buffer | ≥0.23 |
| Water for Injection, USP | Vehicle | Q.S to 1 mL |

Example 19: Medroxyprogesterone Acetate Compositions

The quantitative composition and function of each component in an exemplary embodiment of the disclosure is provided in Table 25.

TABLE 25

Unit composition in medroxyprogesterone acetate compositions

| Ingredients | Function of Components | Concentration (mg/mL) |
|---|---|---|
| MPA, USP | API | 300 |
| Polyethylene glycol 3350 NF | Suspending Agent | 15-30 |
| Docusate sodium, USP | Surfactant | 0.6-1.3 |
| Sodium sulfate anhydrous, USP | Tonicity Adjuster | 10-13 |
| L-Methionine, USP | Stabilizer | 1.5 |
| Monobasic sodium phosphate, Anhydrous, USP | Buffer | ≥0.6 |
| Dibasic Sodium phosphate Anhydrous, USP | Buffer | ≥0.23 |
| Water for Injection, USP | Vehicle | Q.S to 1 mL |

Example 20: Alternative Sterilization Procedure

Compositions can be prepared by dissolving all of the excipients in water for injection (WFI) and filtering the solution into another pre-sterilized tank. To this solution, dispensed medroxyprogesterone acetate is added in small increments with continuous mixing Prior to final weight make up with water for injection through a sterile filter, the pH of the suspension is measured and adjusted if needed with 0.1 N HCl or 0.1 N NaOH (through pH filter). Previously prepared suspension is continuously mixed during filling into vials and/or syringes and/or cartridges. The filled units (vials/syringes/cartridges) are steam sterilized for a minimum of 15 minutes at 122° C. After steam sterilization, the filled units (vials/syringes/cartridges) are cooled to room temperature. The entire batch of finished drug product undergoes manual visual inspection for defects and then is stored in quarantine area until released.

Example 21: Optimization of Excipients

The minimum and maximum concentration (mg/ml) and percent weight/volume (% (w/v)) values for each component in exemplary embodiments of the disclosure are provided in Table 26.

TABLE 26

Unit composition in preferred medroxyprogesterone acetate compositions

| | MIN | | MAX | |
|---|---|---|---|---|
| Ingredients | mg/ml | % (w/v) | mg/ml | % (w/v) |
| Polyethylene glycol 3350 NF | 10 | 1 | 40 | 4 |
| Docusate sodium, USP | 0.6 | 0.06 | 1.5 | 0.15 |
| MPA, USP | 300 | 30 | 400 | 40 |
| Sodium sulfate anhydrous, USP | 10 | 1.0 | 15 | 1.5 |
| L-Methionine, USP | 1.5 | 0.15 | 1.5 | 0.15 |

TABLE 26-continued

Unit composition in preferred medroxyprogesterone acetate compositions

| Ingredients | MIN | | MAX | |
|---|---|---|---|---|
| | mg/ml | % (w/v) | mg/ml | % (w/v) |
| Dibasic sodium phosphate, Anh., USP | 0.23 | 0.023 | 0.52 | 0.052 |
| Monobasic Sodium phosphate Anh., USP | 0.25 | 0.025 | 0.6 | 0.06 |
| Water for Injection, USP | QS to 1 ml | QS to 1 ml | QS to 1 ml | QS to 1 ml |

Several response parameters were tested for the compositions in Table 26, including resuspendability, sedimentation rate, zeta, PSD and osmolality. Other parameters that may be tested include in vitro release (IVR), viscosity and API soluble fraction.

Example 22: Long Duration Stability Testing

The formulations presented in examples 1 and 2, example 4 and examples 11-19 were tested under various conditions for stability over time.

Table 27 provides the storage conditions, stress stability parameters and time intervals used to test the stability of the formulations in the Uniject™ containers.

TABLE 27

Storage conditions and time intervals

| Storage conditions | Time interval (months) | | | | | | | |
|---|---|---|---|---|---|---|---|---|
| | 0 Start | 3 | 6 | 12 | 18 | 24 | 36 | 48 | 60 |
| 25° C./60% RH | x | | | (x→) | | | | | |
| 30° C./75% RH | | x* | x | x | x* | x | x | x | x |
| 40° C./75% RH | | x* | x | | | | | | | x - all required parameters will be analyzed
(x→) - samples will be stored at specified conditions and analyzed when necessary
x* - only appearance, resuspendability, syringeability, content uniformity of the delivered dose and particle size distribution will be analyzed Content uniformity of the delivered dose is based on the assay of the drug substance content of individual units. Preparation of the sample solution was achieved by resuspending the product by vigorously shaking Uniject™ containers until complete resuspension before use and transferring the content of appropriate number of Uniject™ containers into adequate volumetric flasks. The next step was diluting with diluent to reach a final sample concentration of 0.4 to 0.6 mg/mL, sonicating if necessary to dissolve all solids during dilution, allowing cooling to room temperature after sonication.

Sedimentation volume was assessed by resuspending the product by vigorously shaking Uniject™ containers until complete resuspension before use and placing adequate volume of suspension in graduated cylinder. The volume of the sediment is noted at appropriate time points, until equilibrium is reached. The sedimentation volume is calculated by the equation F=Vsed/Vtot, where F is the sedimentation volume, Vsed is the volume of the sediment after equilibrium is reached and Vtot is the total volume of the resuspended suspension.

Example 23—Pharmacokinetics 12 women were sequentially administered medroxyprogesterone acetate. PK was evaluated for at least 182 days. The composition tested was an embodiment of the disclosure and included 400 mg/ml MPA,

TABLE 28

Additional PK Parameter Estimates

| Parameters | N | Mean (Median) | SD (% CV) | Min-Max |
|---|---|---|---|---|
| Cmax (ng/mL) | 6 | 0.53 (0.55) | 0.10 (19.32) | 0.42-0.69 |
| Tmax (days) | 6 | 17.45 (9.49) | 18.67 (106.98) | 1.96-40.96 |
| C28 (ng/mL) | 6 | 0.36 (0.34) | 0.07 (19.93) | 0.03-0.50 |
| C91 (ng/mL) | 6 | 0.41 (0.42) | 0.13 (31.98) | 0.26-0.63 |
| C182 (ng/mL) | 6 | 0.22 (0.20) | 0.08 (37.70) | 0.14-0.34 |
| $AUC_{0-28}$ (days*ng/mL) | 6 | 9.84 (9.31) | 2.48 (25.19) | 7.83-14.52 |
| $AUC_{0-91}$ (days*ng/mL) | 6 | 34.52 (34.87) | 6.72 (19.47) | 23.41-44.06 |
| $AUC_{0-182}$ (days*ng/mL) | 6 | 60.21 (60.28) | 15.11 (25.09) | 38.62-84.88 |
| Half-life (days) | 6 | 99.42 (103.50) | 62.93 (63.29) | 22.92-165.96 |

The compositions were further optimized.

Example 24—Development of Compositions for Increased Duration of Action and Stability Compositions were optimized by assessing a number of parameters in vivo and in vitro. A Design of Experiment (DoE) analysis was performed, using the IMP 13.2.1 mathematical software. Certain ingredients were constant throughout all DoE formulations (Table 29).

TABLE 29

Formulation optimization 300 mg/ml and 400 mg/ml; constant ingredients

| Ingredients constant through all DoE formulations | mg/ml |
|---|---|
| L-Methionine | 1.5 |
| Dibasic sodium phosphate, anhydrous | 0.23 |
| Monobasic sodium phosphate, anhydrous | 0.60 |
| Water for injection | q.s. to 1 mL |

Based on input of concentration ranges for DSS (1.3 to 2.8 mg/mL), PEG3350 (15 to 30 mg/mL) and sodium sulfate (5 to 20 mg/mL), for a fixed 400 mg/ml MPA concentration, sixteen formulations were generated. The formulations were manufactured and tested for one or more of the parameters IVR, resuspendability, sedimentation rate, viscosity, zeta, API soluble fraction, PSD and osmolality. Target resuspendability was not more than 30 seconds, target osmolality was not more than 390 mOsm/kg, and target particle size distribution D(90) was not more than 40 μm. Two parameters for assessing stability are resuspendability of not more than 30 seconds and passing the syringeability test. Select formulations were prepared and tested for stability as described in Example 4.

Results and conclusions: Sodium sulfate and PEG concentrations appear to have the most impact on the sedimentation volume after 7 days (p<0.1) and osmolality, whereas sodium sulfate concentration has a strong influence on resuspendability and DSS and PEG concentrations appear to have the most impact on the Zeta potential (p<0.1). All sixteen samples had the same particle size distribution. Based on an analysis of the concentrations, the formulations in Table 3 will have the greatest duration and stability, and best resuspendability. Table 30 provides measured values for resuspendability, syringeability, injectability, osmolality and sedimentation volume for each of the formulations in Table 3 (400 mg/ml MPA in Ex. 4).

TABLE 30

|  | 96A | 97A | 98A | 99A |
| --- | --- | --- | --- | --- |
| Resuspendability (s) | 10 | 10 | 10 | 10 |
| Syringeability (pass/does not pass) | Pass | Pass | Pass | Pass |
| Osmolality, mOsm/kg | 389 | 397 | 413 | 419 |
| Sedimentation volume (%) | 70 | 56 | 60 | 60 |

A second set of DoE was performed as above, for a fixed 300 mg/ml MPA concentration. The sixteen formulations were manufactured and tested as detailed supra.

Results and conclusions: sodium sulfate and DSS concentrations appear to have the biggest impact (p<0.05) on the sedimentation volume after 7 days, whereas sodium sulfate and PEG concentrations have the most impact on osmolality. DSS and sodium sulfate concentrations have the greatest impact (p<0.1) on Zeta potential. Based on an analysis of the concentrations, the formulations in Table 4 appear to have the potential for greatest duration and stability. Table 31 provides measured values for resuspendability, syringeability, osmolality, sedimentation volume, and zeta potential for each of the formulations in Table 4 (Ex 4).

TABLE 31

|  | 132A | 133A | 134A | 135A |
| --- | --- | --- | --- | --- |
| Resuspendability (s) | 14 | 10 | 10 | 10 |
| Syringeability (pass/does not pass) | pass | pass | pass | pass |
| Osmolality, mOsm/kg | 363 | 296 | 366 | 297 |
| Sedimentation volume (%) | 47 | 40 | 40 | 34 |
| Zeta potential (mV) | −34 | −34 | −41 | −41 |

Formulations suitable for subcutaneous injection, having higher concentrations of active pharmaceutical ingredient, e.g., medroxyprogesterone acetate at about 300 mg/ml to 400 mg/ml, that are suitable for use in regions having high humidity, high temperatures, unreliable access to electricity, and unreliable access to refrigeration will have a resuspendability of not more than 30 seconds. Alternatively, or in addition to a resuspendability of not more than 30 seconds, the formulations will pass the syringeability test. In some embodiments, these formulations have an osmolality of not more than (NMT) about 420 mOsm/kg. Alternatively, or in addition to either a resuspendability of not more than 30 seconds and/or an osmolality of not more than 390 mOsm/kg, these formulations have a particle size distribution D(90) of not more than 40 μm.

For example, in some aspects, the compositions of the disclosure for use in regions having high humidity, high temperatures, unreliable access to electricity, and unreliable access to refrigeration that are suitable for subcutaneous injection comprise about 400 mg/ml of MPA, about 20 to 28 mg/ml of polyethylene glycol, and 0.6 to 1.3 mg/mL of docusate sodium and exhibit a resuspendability of not more than 30 seconds, an osmolality of about 390 mOsm/kg to about 420 mOsm/kg. In some aspects, these compositions exhibit a sedimentation volume of between 55 and 70%. In some aspects, the zeta potential of these compositions in between −35 and −45 mV.

For example, in some aspects, the compositions of the disclosure for use in regions having high humidity, high temperatures, unreliable access to electricity, and unreliable access to refrigeration that are suitable for subcutaneous injection comprise about 300 mg/ml of MPA, about 20 mg/ml of polyethylene glycol, and 0.6 to 1 mg/mL of docusate sodium and exhibit a resuspendability of not more than 30 seconds, an osmolality of about 295 mOsm/kg to about 365 mOsm/kg. In some aspects, these compositions exhibit a sedimentation volume of between 30 and 50%. In some aspects, the zeta potential of these compositions in between −35 and −45 mV.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention. More specifically, it will be apparent that certain solvents which are both chemically and physiologically related to the solvents disclosed herein may be substituted for the solvents described herein while the same or similar results would be achieved. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications are herein incorporated by reference to the same extent as if each individual publication was specifically and individually indicated to be incorporated by reference. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An aqueous composition for subcutaneous injection comprising medroxyprogesterone acetate at a concentration of about 260 mg/ml to 440 mg/ml, docusate sodium at a concentration of about 0.6 mg/ml to 1.5 mg/ml, and polyethylene glycol.

2. The composition according to claim 1, wherein the concentration of polyethylene glycol is about 10 mg/ml to 40 mg/ml, or about 15 mg/ml to 30 mg/ml.

3. The composition according to claim 1, wherein the polyethylene glycol is polyethylene glycol 3350.

4. The composition according to claim 1, further comprising a sulfate salt or a sodium salt or a sulfate salt and a sodium salt.

5. The composition according to claim 4, wherein the composition comprises a sulfate salt being sodium sulfate.

6. The composition according to claim 1, further comprises a stabilizer selected from methionine, thioglycerol, monothioglycerol, lipoic acid, propyl gallate, cysteine, sodium formaldehyde sulfoxylate, or dihydrolipoic acid.

7. The composition according to claim 1, further comprising a buffering salt selected from a phosphate salt or a combination of phosphate salts.

8. The composition according to claim 7, wherein the buffering salt is monobasic sodium phosphate, dibasic sodium phosphate, or a combination thereof.

9. The composition according to claim 1, having a pH of about 4.0 to about 7.0, or having a pH of about 6.0 to about 7.0, or about 6.0.

10. The composition according to claim 1, comprising sodium sulfate, methionine, monobasic sodium phosphate, and dibasic sodium phosphate.

11. The composition according to claim 1, wherein the concentration of medroxyprogesterone acetate is about 400 mg/ml.

12. The composition according to claim 1, wherein the concentration of medroxyprogesterone acetate is about 300 mg/ml.

13. The composition according to claim 1, wherein the concentration of docusate sodium is about 0.6 mg/ml to about 1.3 mg/ml, about 0.6 mg/ml, about 1.0 mg/ml or about 1.3 mg/ml.

14. The composition according to claim 13, wherein the concentration of docusate sodium is about 0.6 mg/ml or about 1.0 mg/ml.

15. The composition according to claim 1, wherein the concentration of polyethylene glycol is about 20 mg/ml to about 28 mg/ml.

16. The composition according to claim 15, wherein the concentration of polyethylene glycol is about 20 mg/ml or about 28 mg/ml.

17. The composition according to claim 1, further comprising one or more excipients selected from anhydrous sodium sulfate, L-methionine, anhydrous dibasic sodium phosphate, and anhydrous monobasic sodium phosphate.

18. The composition according to claim 1, wherein the composition is stable for at least 36 months under stress conditions.

19. A method for preventing pregnancy or for treating endometriosis-associated pain or endometrial carcinoma in a female subject, or treating renal carcinoma in a subject in need thereof, the method comprising subcutaneously administering to the subject a composition according to claim 1.

20. The method according to claim 19, wherein the composition is administered once every four months to once every 6 months.

21. The composition according to claim 17, comprising anhydrous sodium sulfate, L-methionine, anhydrous dibasic sodium phosphate, and anhydrous monobasic sodium phosphate.

22. The composition according to claim 20, wherein the composition is administered once every six months.

* * * * *